United States Patent
Tang et al.

(10) Patent No.: US 10,704,034 B2
(45) Date of Patent: Jul. 7, 2020

(54) POLYPEPTIDES HAVING XYLANASE ACTIVITY AND POLYNUCLEOTIDES ENCODING SAME

(71) Applicant: Novozymes Inc., Davis, CA (US)

(72) Inventors: Lan Tang, Beijing (CN); Ye Liu, Beijing (CN); Yu Zhang, Beijing (CN); Junxin Duan, Beijing (CN)

(73) Assignee: Novozymes Inc., Davis, CA (US)

( * ) Notice: Subject to any disclaimer, the term of this patent is extended or adjusted under 35 U.S.C. 154(b) by 1876 days.

(21) Appl. No.: 14/346,227

(22) PCT Filed: Oct. 26, 2012

(86) PCT No.: PCT/CN2012/083618
§ 371 (c)(1),
(2) Date: Mar. 20, 2014

(87) PCT Pub. No.: WO2013/060293
PCT Pub. Date: May 2, 2013

(65) Prior Publication Data
US 2014/0220642 A1     Aug. 7, 2014

Related U.S. Application Data

(60) Provisional application No. 61/565,782, filed on Dec. 1, 2011.

(30) Foreign Application Priority Data

Oct. 28, 2011   (WO) ................ PCT/CN2011/081495

(51) Int. Cl.
*C12N 9/24*   (2006.01)
*C12P 19/14*   (2006.01)
*C12P 19/02*   (2006.01)

(52) U.S. Cl.
CPC ............ *C12N 9/2482* (2013.01); *C12P 19/02* (2013.01); *C12P 19/14* (2013.01); *C12Y 302/01008* (2013.01); *C12P 2203/00* (2013.01)

(58) Field of Classification Search
None
See application file for complete search history.

(56) References Cited

U.S. PATENT DOCUMENTS

2009/0042266 A1   2/2009   Vehmaanpera et al.
2011/0045544 A1   2/2011   Vehmaanpera et al.

FOREIGN PATENT DOCUMENTS

| WO | 1997027292 A1 | 7/1997 |
| WO | WO-2009033071 A2 * | 3/2009 |
| WO | 2011/041405 A1 | 4/2011 |
| WO | WO-2011041405 A1 * | 4/2011 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
WO 2011-038019 A2—Geneseq Access No. AZG45552.
Furniss et al, 2005, J Sci Food Agric 85, 574-58.
Berka et al., Genbank Accession No. AEO63155 (2011).
Berka et al., Genbank Accession No. AEO63459 (2011).
Birren et al., Genbank Accession No. XP_001226236 (2008).
Birren et al., Genbank Accession No. XP_001230196 (2008).
Espagne et al., Genbank Accession No. XP_001911839 (2010).
Maisuradze et al., Genbank Accession No. ACP27611 (2011).
Nierman et al., Genbank Accession No. XP_751237 (2008).
Vaillancourt et al., Genbank Accession No. EFQ33770 (2010).
Van Gool et al., Genbank Accession No. AEN99940 (2011).

* cited by examiner

*Primary Examiner* — Iqbal H Chowdhury
(74) *Attorney, Agent, or Firm* — David Fazzolare

(57) ABSTRACT

The present invention provides isolated polypeptides having xylanase activity and polynucleotides encoding the polypeptides. The invention also provides nucleic acid constructs, vectors, and host cells comprising the polynucleotides as well as methods of producing and using the polypeptides.

19 Claims, 10 Drawing Sheets

Specification includes a Sequence Listing.

US 10,704,034 B2

POLYPEPTIDES HAVING XYLANASE ACTIVITY AND POLYNUCLEOTIDES ENCODING SAME

CROSS-REFERENCE TO RELATED APPLICATIONS

This application is a 35 U.S.C. 371 national application of PCT/CN2012/083618 filed Oct. 26, 2012 which claims priority or the benefit under 35 U.S.C. 119 of Chinese PCT application no. PCT/CN2011/081495 filed Oct. 28, 2011 and U.S. provisional application no. 61/565,782 filed Dec. 1, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having xylanase activity and polynucleotides encoding the polypeptides. The invention also relates to nucleic acid constructs, vectors, and host cells comprising the polynucleotides as well as methods of producing and using the polypeptides.

Description of the Related Art

Lignocellulose, the world's largest renewable biomass resource, is composed mainly of lignin, cellulose, and hemicellulose, of which a large part of the latter is xylan. Xylanases (e.g., endo-1,4-beta-xylanase, EC 3.2.1.8) hydrolyze internal β-1,4-xylosidic linkages in xylan to produce smaller molecular weight xylose and xylo-oligomers. Xylans are polysaccharides formed from 1,4-β-glycoside-linked D-xylopyranoses.

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Once the cellulose is converted to glucose, the glucose can easily be fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art to improve cellulolytic enzyme compositions through supplementation with additional enzymes to increase efficiency and to provide cost-effective enzyme solutions for degradation of lignocellulose.

WO 2011/041405 discloses a GH10 xylanase and gene thereof from *Penicillium pinophilum*.

The present invention provides polypeptides having xylanase activity and polynucleotides encoding the polypeptides.

SUMMARY OF THE INVENTION

The present invention relates to isolated polypeptides having xylanase activity selected from the group consisting of:

(a) a polypeptide having at least 60% sequence identity to the mature polypeptide of SEQ ID NO: 2; at least 65% sequence identity to the mature polypeptide of SEQ ID NO: 12; at least 70% sequence identity to the mature polypeptide of SEQ ID NO: 4 or SEQ ID NO: 10; at least 75% sequence identity to the mature polypeptide of SEQ ID NO: 14 or SEQ ID NO: 16; at least 80% sequence identity to the mature polypeptide of SEQ ID NO: 6 or SEQ ID NO: 8; at least 85% sequence identity to the mature polypeptide of SEQ ID NO: 20; or at least 90% sequence identity to the mature polypeptide of SEQ ID NO: 18;

(b) a polypeptide encoded by a polynucleotide that hybridizes under at least medium-high stringency conditions with (i) the mature polypeptide coding sequence of SEQ ID NO: 1, SEQ ID NO: 3, SEQ ID NO: 9, or SEQ ID NO: 11, (ii) the cDNA sequence of SEQ ID NO: 1, SEQ ID NO: 3, SEQ ID NO: 9, or SEQ ID NO: 11, or (iii) the full-length complement of (i) or (ii); or at least high stringency conditions with (i) the mature polypeptide coding sequence of SEQ ID NO: 5, SEQ ID NO: 7, SEQ ID NO: 13, SEQ ID NO: 15, SEQ ID NO: 17, or SEQ ID NO: 19, (ii) the cDNA sequence of SEQ ID NO: 5, SEQ ID NO: 13, SEQ ID NO: 17, or SEQ ID NO: 19, or (iii) the full-length complement of (i) or (ii);

(c) a polypeptide encoded by a polynucleotide having at least 60% sequence identity to the mature polypeptide coding sequence of SEQ ID NO: 1 or the cDNA sequence thereof; at least 65% sequence identity to the mature polypeptide coding sequence of SEQ ID NO: 11 or the cDNA sequence thereof; at least 70% sequence identity to the mature polypeptide coding sequence of SEQ ID NO: 3 or the cDNA sequence thereof or SEQ ID NO: 9 or the cDNA sequence thereof; at least 75% sequence identity to the mature polypeptide coding sequence of SEQ ID NO: 13 or the cDNA sequence thereof or the mature polypeptide coding sequence of SEQ ID NO: 15; at least 80% sequence identity to the mature polypeptide coding sequence of SEQ ID NO: 5 or the cDNA sequence thereof or the mature polypeptide coding sequence of SEQ ID NO: 7; at least 85% sequence identity to the mature polypeptide coding sequence of SEQ ID NO: 19 or the cDNA sequence thereof; or at least 90% sequence identity to the mature polypeptide coding sequence of SEQ ID NO: 17 or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 comprising a substitution, deletion, and/or insertion at one or more (e.g., several) positions; and (e) a fragment of the polypeptide of (a), (b), (c), or (d) that has xylanase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading a cellulosic or xylan-containing material, comprising: treating the cellulosic or xylan-containing material with an enzyme composition in the presence of a polypeptide having xylanase activity of the present invention. In one aspect, the processes further comprise recovering the degraded or converted cellulosic or xylan-containing material.

The present invention also relates to processes of producing a fermentation product, comprising: (a) saccharifying a cellulosic or xylan-containing material with an enzyme composition in the presence of a polypeptide having xylanase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having xylanase activity of the present invention. In one aspect, the fermenting of the cellulosic or xylan-containing material produces a fermentation product. In another aspect, the processes further comprise recovering the fermentation product from the fermentation.

The present invention also relates to a polynucleotide encoding a signal peptide comprising or consisting of amino acids 1 to 20 of SEQ ID NO: 2, amino acids 1 to 17 of SEQ ID NO: 4, amino acids 1 to 18 of SEQ ID NO: 6, amino acids 1 to 22 of SEQ ID NO: 8, amino acids 1 to 18 of SEQ ID NO: 10, amino acids 1 to 20 of SEQ ID NO: 12, amino acids 1 to 17 of SEQ ID NO: 14, amino acids 1 to 19 of SEQ ID NO: 16, amino acids 1 to 17 of SEQ ID NO: 18, or amino acids 1 to 17 of SEQ ID NO: 20, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
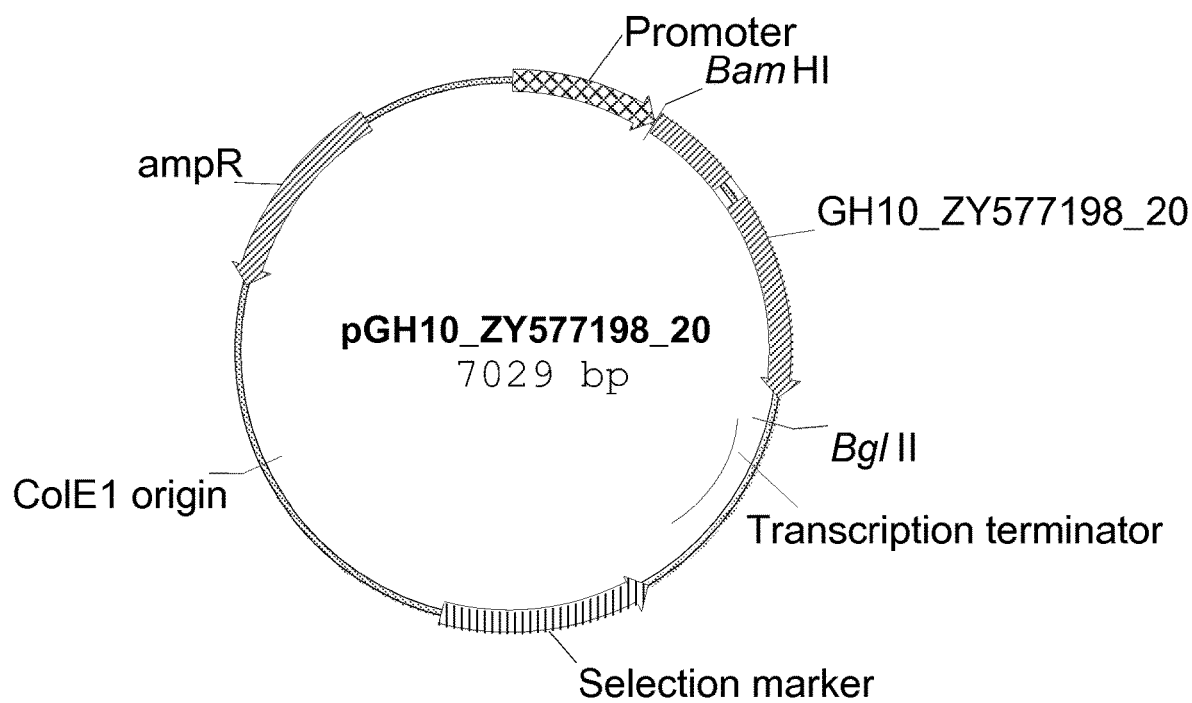
FIG. 1 shows a restriction map of plasmid pGH10_ZY577198_20.

Acetylxylan esterase: The term "acetylxylan esterase" means a carboxyl esterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, J. Basic Microbiol. 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has xylanase activity. In one aspect, a fragment contains at least 330 amino acid residues, e.g., at least 350 amino acid residues or at least 370 amino acid residues of SEQ ID NO: 2. In another aspect, a fragment contains at least 300 amino acid residues, e.g., at least 315 amino acid residues or at least 330 amino acid residues of SEQ ID NO: 4. In another aspect, a fragment contains at least 300 amino acid residues, e.g., at least 320 amino acid residues or at least 340 amino acid residues of SEQ ID NO: 6. In another aspect, a fragment contains at least 300 amino acid residues, e.g., at least 315 amino acid residues or at least 330 amino acid residues of SEQ ID NO: 8. In another aspect, a fragment contains at least 260 amino acid residues, e.g., at least 275 amino acid residues or at least 290 amino acid residues of SEQ ID NO: 10. In one aspect, a fragment contains at least 290 amino acid residues, e.g., at least 305 amino acid residues or at least 320 amino acid residues of SEQ ID NO: 12. In another aspect, a fragment contains at least 290 amino acid residues, e.g., at least 305 amino acid residues or at least 320 amino acid residues of SEQ ID NO: 14. In another aspect, a fragment contains at least 300 amino acid residues, e.g., at least 315 amino acid residues or at least 330 amino acid residues of SEQ ID NO: 16. In another aspect, a fragment contains at least 320 amino acid residues, e.g., at least 335 amino acid residues or at least 350 amino acid residues of SEQ ID NO: 18. In another aspect, a fragment contains at least 300 amino acid residues, e.g., at least 315 amino acid residues or at least 330 amino acid residues of SEQ ID NO: 20.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y.

Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 406 of SEQ ID NO: 2 (P244XT) based on the SignalP program (Nielsen et al., 1997, *Protein Engineering* 10:1-6) that predicts amino acids 1 to 20 of SEQ ID NO: 2 are a signal peptide. In another aspect, the mature polypeptide is amino acids 18 to 360 of SEQ ID NO: 4 (P244XW) based on the SignalP program that predicts amino acids 1 to 17 of SEQ ID NO: 4 are a signal peptide. In another aspect, the mature polypeptide is amino acids 19 to 376 of SEQ ID NO: 6 (P244Y1) based on the SignalP program that predicts amino acids 1 to 18 of SEQ ID NO: 6 are a signal peptide. In another aspect, the mature polypeptide is amino acids 23 to 367 of SEQ ID NO: 8 (P244Y2) based on the SignalP program that predicts amino acids 1 to 22 of SEQ ID NO: 8 are a signal peptide. In another aspect, the mature polypeptide is amino acids 19 to 326 of SEQ ID NO: 10 (P23DM4) based on the SignalP program that predicts amino acids 1 to 18 of SEQ ID NO: 10 are a signal peptide. In another aspect, the mature polypeptide is amino acids 21 to 354 of SEQ ID NO: 12 (P249XY) based on the SignalP program that predicts amino acids 1 to 20 of SEQ ID NO: 12 are a signal peptide. In another aspect, the mature polypeptide is amino acids 18 to 355 of SEQ ID NO: 14 (P24MCW) based on the SignalP program that predicts amino acids 1 to 17 of SEQ ID NO: 14 are a signal peptide. In another aspect, the mature polypeptide is amino acids 20 to 366 of SEQ ID NO: 16 (P24MCX) based on the SignalP program that predicts amino acids 1 to 19 of SEQ ID NO: 16 are a signal peptide. In another aspect, the mature polypeptide is amino acids 18 to 381 of SEQ ID NO: 18 (P24FVF) based on the SignalP program that predicts amino acids 1 to 17 of SEQ ID NO: 18 are a signal peptide. In another aspect, the mature polypeptide is amino acids 18 to 362 of SEQ ID NO: 20 (P241KU) based on the SignalP program that predicts amino acids 1 to 17 of SEQ ID NO: 20 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 61 to 1311 of SEQ ID NO: 1 (D822JR) or the cDNA sequence thereof based on the SignalP program (Nielsen et al., 1997, supra) that predicts nucleotides 1 to 60 of SEQ ID NO: 1 encode a signal peptide. In another aspect, the mature polypeptide coding sequence is nucleotides 52 to 1347 of SEQ ID NO: 3 (D822JT) or the cDNA sequence thereof based on the SignalP program that predicts nucleotides 1 to 51 of SEQ ID NO: 3 encode a signal peptide. In another aspect, the mature polypeptide coding sequence is nucleotides 55 to 1196 of SEQ ID NO: 5 (D822JW) or the cDNA sequence thereof based on the SignalP program that predicts nucleotides 1 to 54 of SEQ ID NO: 5 encode a signal peptide. In another aspect, the mature polypeptide coding sequence is nucleotides 67 to 1101 of SEQ ID NO: 7 (D822JX) or the cDNA sequence thereof based on the SignalP program that predicts nucleotides 1 to 66 of SEQ ID NO: 7 encode a signal peptide. In another aspect, the mature polypeptide coding sequence is nucleotides 55 to 1620 of SEQ ID NO: 9 (D6RM) or the cDNA sequence thereof based on the SignalP program that predicts nucleotides 1 to 54 of SEQ ID NO: 9 encode a signal peptide. In another aspect, the mature polypeptide coding sequence is nucleotides 61 to 1362 of SEQ ID NO: 11 (D82 DB2) or the cDNA sequence thereof based on the SignalP program that predicts nucleotides 1 to 60 of SEQ ID NO: 11 encode a signal peptide. In another aspect, the mature polypeptide coding sequence is nucleotides 52 to 1510 of SEQ ID NO: 13 (D1316T) or the cDNA sequence thereof based on the SignalP program that predicts nucleotides 1 to 51 of SEQ ID NO: 13 encode a signal peptide. In another aspect, the mature polypeptide coding sequence is nucleotides 58 to 1098 of SEQ ID NO: 15 (D1315U) or the cDNA sequence thereof based on the SignalP program that predicts nucleotides 1 to 57 of SEQ ID NO: 15 encode a signal peptide. In another aspect, the mature polypeptide coding sequence is nucleotides 52 to 1362 of SEQ ID NO: 17 (D82PQC) or the cDNA sequence thereof based on the SignalP program that predicts nucleotides 1 to 51 of SEQ ID NO: 17 encode a signal peptide. In another aspect, the mature polypeptide coding sequence is nucleotides 52 to 1165 of SEQ ID NO: 19 (D72UED) or the cDNA sequence thereof based on the SignalP program that predicts nucleotides 1 to 51 of SEQ ID NO: 19 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity. In one aspect, a subsequence contains at least 990 nucleotides, e.g., at least 1050 nucleotides or at least 1110 nucleotides of SEQ ID NO: 1. In another aspect, a subsequence contains at least 900 nucleotides, e.g., at least 945 nucleotides or at least 990 nucleotides of SEQ ID NO: 3. In another aspect, a subsequence contains at least 900 nucleotides, e.g., at least 960 nucleotides or at least 1020 nucleotides of SEQ ID NO: 5. In another aspect, a subsequence contains at least 900 nucleotides, e.g., at least 945 nucleotides or at least 990 nucleotides of SEQ ID NO: 7. In another aspect, a subsequence contains at least 780 nucleotides, e.g., at least 825 nucleotides or at least 870 nucleotides of SEQ ID NO: 9. In another aspect, a subsequence contains at least 870 nucleotides, e.g., at least 915 nucleotides or at least 960 nucleotides of SEQ ID NO: 11. In another aspect, a subsequence contains at least 870 nucleotides, e.g., at least 915 nucleotides or at least 960 nucleotides of SEQ ID NO: 13. In another aspect, a subsequence contains at least 900 nucleotides, e.g., at least 945 nucleotides or at least 990 nucleotides of SEQ ID NO: 15. In another aspect, a subsequence contains at least 960 nucleotides, e.g., at least 1005 nucleotides or at least 1050 nucleotides of SEQ ID NO: 17. In another aspect, a subsequence contains at least 900 nucleotides, e.g., at least 945 nucleotides or at least 990 nucleotides of SEQ ID NO: 19.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase-Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity can be determined with 0.2% AZCL-arabinoxylan as substrate in 0.01% TRITON® X-100 and 200 mM sodium phosphate buffer pH 6 at 37° C. or 0.2% AZCL-xylan as substrate in 0.01% TRITON® X-100 and 20 mM sodium acetate buffer pH 5.0 at 50° C. (see Example 17). One unit of xylanase activity is defined as 1.0 mmole of azurine produced per minute at 37° C., pH 6 from 0.2% AZCL-arabinoxylan as substrate in 200 mM sodium phosphate pH 6 or at 50° C., pH 5 from 0.2% AZCL-xylan as substrate in 20 mM sodium acetate pH 5. Alternatively, the xylanase activity can be determined using birchwood xylan as substrate according to Example 16.

The polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20.

DETAILED DESCRIPTION OF THE INVENTION

Polypeptides Having Xylanase Activity

In an embodiment, the present invention relates to isolated polypeptides having a sequence identity to the mature polypeptide of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 12 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 4 or SEQ ID NO: 10 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 14 or SEQ ID NO: 16 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 6 or SEQ ID NO: 8 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 20 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 18 of at least 90%, e.g., at least 91%, at least 92%, at least 93%, at least 94%, at least 95%, at least 96%, at least 97%, at least 98%, at least 99%, or 100%; which have xylanase activity. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 or an allelic variant thereof; or is a fragment thereof having xylanase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20. In another aspect, the polypeptide comprises or consists of amino acids 21 to 406 of SEQ ID NO: 2, amino acids 18 to 360 of SEQ ID NO: 4, amino acids 19 to 376 of SEQ ID NO: 6, amino acids 23 to 367 of SEQ ID NO: 8, amino acids 19 to 326 of SEQ ID NO: 10, amino acids 21 to 354 of SEQ ID NO: 12, amino acids 18 to 355 of SEQ ID NO: 14, amino acids 20 to 366 of SEQ ID NO: 16, amino acids 18 to 381 of SEQ ID NO: 18, or amino acids 18 to 362 of SEQ ID NO: 20.

In another embodiment, the present invention relates to an isolated polypeptide having xylanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19, (ii) the cDNA sequence of SEQ ID NO: 1, SEQ ID NO: 3, SEQ ID NO: 5, SEQ ID NO: 9, SEQ ID NO: 11, SEQ ID NO: 13, SEQ ID NO: 17, or SEQ ID NO: 19, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19, or a subsequence thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20, the mature polypeptide thereof, or a fragment thereof, may be used to design nucleic acid probes to identify and clone DNA encoding polypeptides having xylanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19, the mature polypeptide coding sequences thereof, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19; (ii) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19; (iii) the cDNA sequence of SEQ ID NO: 1, SEQ ID NO: 3, SEQ ID NO: 5, SEQ ID NO: 9, SEQ ID NO: 11, SEQ ID NO: 13, SEQ ID NO: 17, or SEQ ID NO: 19; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19; or the cDNA sequence of SEQ ID NO: 1, SEQ ID NO: 3, SEQ ID NO: 5, SEQ ID NO: 9, SEQ ID NO: 11, SEQ ID NO: 13, SEQ ID NO: 17, or SEQ ID NO: 19.

In another embodiment, the present invention relates to an isolated polypeptide having xylanase activity encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 11 or the cDNA sequence thereof of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 3 or the cDNA sequence thereof or the mature polypeptide coding sequence of SEQ ID NO: 9 or the cDNA sequence thereof of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 13 or the cDNA sequence thereof or the mature polypeptide coding sequence of SEQ ID NO: 15 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 5 or the cDNA sequence thereof or the mature polypeptide coding sequence of SEQ ID NO: 7 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 19 or the cDNA sequence thereof of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 17 or the cDNA sequence thereof of at least 90%, e.g., at least 91%, at least 92%, at least 93%, at least 94%, at least 95%, at least 96%, at least 97%, at least 98%, at least 99%, or 100%; which have xylanase activity.

In another embodiment, the present invention relates to variants of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Xylanase Activity

A polypeptide having xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Scytalidium* polypeptide. In another aspect, the polypeptide is a *Scytalidium thermophilum* polypeptide. In another aspect, the polypeptide is a *Malbranchea* polypeptide. In another aspect, the polypeptide is a *Malbranchea cinnamomea* polypeptide. In another aspect, the polypeptide is a *Corynascus* polypeptide. In another aspect, the polypeptide is a *Corynascus thermophilus* polypeptide. In another aspect, the polypeptide is a *Corynascus thermophilus* CBS 174.70 polypeptide. In another aspect, the polypeptide is a *Penicillium* polypeptide. In another aspect, the polypeptide is a *Penicillium oxalicum* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Scytalidium*, *Malbranchea*, *Corynascus*, or *Penicillium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19, or the cDNA sequence of the mature polypeptide coding sequence of SEQ ID NO: 1, SEQ ID NO: 3, SEQ ID NO: 5, SEQ ID NO: 9, SEQ ID NO: 11, SEQ ID NO: 13, SEQ ID NO: 17, or SEQ ID NO: 19, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei*translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei*translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of agene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus* equi subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Scytalidium thermophilum*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is a *Scytalidium* cell. In another aspect, the cell is a *Scytalidium thermophilum* cell. In another aspect, the cell is a *Malbranchea* cell. In another aspect, the cell is a *Malbranchea cinnamomea* cell. In another aspect, the cell is a *Corynascus* cell. In another aspect, the cell is a *Corynascus thermophilus* cell. In another aspect, the cell is a *Corynascus thermophilus* CBS 174.70 cell. In another aspect, the cell is a *Penicillium* cell. In another aspect, the cell is a *Penicillium oxalicum* cell.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising a polypeptide of the present invention is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and optionally (b) recovering the polypeptide.

Removal or Reduction of Xylanase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions. The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV)

irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having xylanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially xylanase-free product are of particular interest in the production of eukaryotic polypeptides, in particular fungal proteins such as enzymes. The xylanase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from xylanase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having xylanase activity, or compositions thereof.

The present invention also relates to processes for degrading a cellulosic or xylan-containing material, comprising: treating the cellulosic or xylan-containing material with an enzyme composition in the presence of a polypeptide having xylanase activity of the present invention. In one aspect, the processes further comprise recovering the degraded or converted cellulosic or xylan-containing material. Soluble products of degradation or conversion of the cellulosic or xylan-containing material can be separated from insoluble cellulosic or xylan-containing material using a method known in the art such as, for example, centrifugation, filtration, or gravity settling.

The present invention also relates to processes of producing a fermentation product, comprising: (a) saccharifying a cellulosic or xylan-containing material with an enzyme composition in the presence of a polypeptide having xylanase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having xylanase activity of the present invention. In one aspect, the fermenting of the cellulosic or xylan-containing material produces a fermentation product. In another aspect, the processes further comprise recovering the fermentation product from the fermentation.

The processes of the present invention can be used to saccharify the cellulosic or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic or xylan-containing material typically involves pretreatment, enzymatic hydrolysis (saccharification), and fermentation.

The processing of the cellulosic or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or xylan-containing material is heated to disrupt the plant cell wall components, including lignin, hemicellulose, and cellulose to make the cellulose and other fractions, e.g., hemicellulose, accessible to enzymes. The cellulosic or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or xylan-containing material is present during pretreatment in amounts preferably between 10-80 wt %, e.g., 20-70 wt % or 30-60 wt %, such as around 40 wt %. The pretreated cellulosic or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having xylanase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having xylanase activity depend on several factors including, but not limited to, the mixture of cellulolytic and/or hemicellulolytic enzyme components, the cellulosic or xylan-containing material, the concentration of cellulosic or xylan-containing material, the pretreatment(s) of the cellulosic or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic or xylan-containing material.

In another aspect, an effective amount of a polypeptide having xylanase activity to the cellulosic or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or xylan-containing material.

In another aspect, an effective amount of a polypeptide having xylanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter,*

*Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyceslividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Scytalidium thermophilum, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii*endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea*endoglucanase (GENBANK™ accession no. AB003107), *Melanocarpus albomyces*endoglucanase (GENBANK™ accession no. MAL515703), *Neurospora crassa*endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus* aculeatus (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In one aspect, the GH61 polypeptide having cellulolytic enhancing activity is used in the presence of a soluble activating divalent metal cation according to WO 2008/151043, e.g., manganese sulfate or copper sulfate.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH 10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus* clavatus (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, Calif., 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora*

*lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichiastipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR(NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, Water Science and Technology 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 20 of SEQ ID NO: 2, amino acids 1 to 17 of SEQ ID NO: 4, amino acids 1 to 18 of SEQ ID NO: 6, amino acids 1 to 22 of SEQ ID NO: 8, amino acids 1 to 18 of SEQ ID NO: 10, amino acids 1 to 20 of SEQ ID NO: 12, amino acids 1 to 17 of SEQ ID NO: 14, amino acids 1 to 19 of SEQ ID NO: 16, amino acids 1 to 17 of SEQ ID NO: 18, or amino acids 1 to 17 of SEQ ID NO: 20. The polynucleotide may further comprise a gene encoding a protein, which is operably linked to the signal peptide. The protein is preferably foreign to the signal peptide. In one aspect, the polynucleotide encoding the signal peptide is nucleotides 1 to 60 of SEQ ID NO: 1. In another aspect, the polynucleotide encoding the signal peptide is nucleotides 1 to 51 of SEQ ID NO: 3. In another aspect, the polynucleotide encoding the signal peptide is nucleotides 1 to 54 of SEQ ID NO: 5. In another aspect, the polynucleotide encoding the signal peptide is nucleotides 1 to 66 of SEQ ID NO: 7. In another aspect, the polynucleotide encoding the signal peptide is nucleotides 1 to 54 of SEQ ID NO: 9. In another aspect, the polynucleotide encoding the signal peptide is nucleotides 1 to 60 of SEQ ID NO: 11. In another aspect, the polynucleotide encoding the signal peptide is nucleotides 1 to 51 of SEQ ID NO: 13. In another aspect, the polynucleotide encoding the signal peptide is nucleotides 1 to 57 of SEQ ID NO: 15. In another aspect, the polynucleotide encoding the signal peptide is nucleotides 1 to 51 of SEQ ID NO: 17. In another aspect, the polynucleotide encoding the signal peptide is nucleotides 1 to 51 of SEQ ID NO: 19.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strains

A fungal strain designated NN047338 was isolated from a soil sample collected from Hunan province in China by dilution on PDA plates at 45° C. and then purified by transferring a single conidium onto a YG agar plate. The strain NN047338 was identified as *Scytalidium thermophilum*, based on both morphological characteristics and ITS rDNA sequence.

A fungal strain designated NN051564 was isolated from a compost sample on PCS agar plates collected in China. The strain NN051564 was identified as *Malbranchea cinnamomea*, based on both morphological characteristics and ITS rDNA sequence.

A fungal strain designated was isolated from a soil sample collected in China by dilution on PDA plates at 45° C. and then purified by transferring a single conidium onto a YG agar plate. The strain NN044758 was identified as *Malbranchea cinnamomea*, based on both morphological characteristics and ITS rDNA sequence.

A fungal strain designated NN000308 was obtained from Centraalbureau voor Schimmelcultures named as CBS174.70. The strain NN000308 was identified as *Corynascus thermophilus* (synonym *Myceliophthora fergusii*), based on both morphological characteristics and ITS rDNA sequence.

A fungal strain designated NN051380 was isolated from a soil sample collected in China. The strain NN051380 was identified as *Penicillium oxalicum*, based on both morphological characteristics and ITS rDNA sequence.

Media

PDA plates were composed of 39 grams of potato dextrose agar and deionized water to 1 liter.

YG agar plates were composed of 5 g of yeast extract, 10 g of glucose, 20 g of agar, and deionized water to 1 liter.

PCS agar plates were composed of 25 g of PCS, 20 g of agar, 1 g of Bacto Peptone, 5 g of yeast extract, 2.5 g of glucose, 5 g of $NaNO_3$, 3 g of $NH_4Cl$, 2 g of MES, 2.5 g of citric acid, 0.2 g of $CaCl_2 \cdot 2H_2O$, 0.2 g of $MgSO_4 \cdot 7H_2O$, 4 g of $K_2HPO_4$, 1 ml of COVE trace elements solution, and deionized water to 1 liter.

COVE trace elements solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, 10 g of $ZnSO_4 \cdot 7H_2O$, and deionized water to 1 liter.

YPG medium was composed of 0.4% of yeast extract, 0.1% of $KH_2PO_4$, 0.05% of $MgSO_4 \cdot 7H_2O$, and 1.5% glucose in deionized water.

YPM medium was composed of 1% of yeast extract, 2% of peptone, and 2% of maltose in deionized water.

Czapek's medium was composed of 30 g of sucrose, 3 g of $NaNO_3$, 0.5 g of $MgSO_4 \cdot 7H_2O$, 0.01 g of $FeSO_4 \cdot 7H_2O$, 1 g of $K_2HPO_4$ and 0.5 g of KCl in 1 liter final volume of deionized water. The pH was adjusted to pH4 with 1M HCl.

Minimal medium plates were composed of 342 g of sucrose, 20 ml of salt solution, 20 g of agar, and deionized water to 1 liter. The salt solution was composed of 2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

NNCYP-PCS medium was composed of 5.0 g of $NaNO_3$, 3.0 g of $NH_4Cl$, 2.0 g of MES, 2.5 g of citric acid, 0.2 g of $CaCl_2$ $2H_2O$, 1.0 g of Bacto Peptone, 5.0 g of yeast extract, 0.2 g of $MgSO_4$ $7H_2O$, 4.0 g of $K_2HPO_4$, 1.0 ml of COVE trace elements solution, 2.5 g of glucose, 25.0 g of PCS, and deionized water to 1 liter.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

Example 1

Genomic DNA Extraction

*Scytalidium thermophilum* strain NN047338 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNEASY® Plant Maxi Kit (QIAGEN GmbH, Hilden, Germany) following the manufacturer's instructions.

*Malbranchea cinnamomea* NN051564 was inoculated onto a PDA plate and incubated at 37° C. for 4-5 days with shaking at 160 rpm. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit.

*Malbranchea cinnamomea* strain NN044758 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a Large-Scale Column Fungal DNAout (BAOMAN BIOTECHNOLOGY, Shanghai, China) according to the manufacturer's instructions.

*Corynascus thermophilus* strain NN000308 was inoculated onto a PDA plate and incubated for 3 days at 45° C. in the darkness. Several mycelia-PDA plugs were inoculated into 500 ml shake flasks containing 100 ml of YPG medium. The flasks were incubated for 4 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit.

*Penicillium oxalicum* strain NN051380 was inoculated onto a PDA plate and incubated for 5 days at 25° C. in the darkness. Several mycelia-PDA plugs were inoculated into 500 ml shake flasks containing 100 ml of Czapek's medium. The flasks were incubated for 3 days at 30° C. with shaking at 160 rpm. The mycelia were collected by filtration through MIRACLOTH® and frozen in liquid nitrogen. Frozen mycelia were ground, by a mortar and a pestle, to a fine powder, and the genomic DNA was isolated using a DNEASY® Plant Maxi Kit.

Example 2

Identification of a *Malbranchea cinnamomea* Strain NN051564 GH10 Xylanase Coding Sequence A *Malbranchea cinnamomea* GH10 xylanase coding sequence was identified by transposon assisted signal trapping of a cDNA library of *Malbranchea cinnamomea* strain NN051564.

The *Malbranchea cinnamomea* strain was inoculated onto a PDA plate and incubated for 4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 3, day 4, day 5, and day 6, respectively. Then the mycelia from each day was frozen in liquid nitrogen and stored in a −80° C. freezer until use. The frozen mycelia were transferred into a liquid nitrogen prechilled mortar and pestle and ground to a fine powder. Total RNA was prepared from the powdered mycelia of each day by extraction with TRIzol reagent (Invitrogen Corporation, Carlsbad, Calif., USA). The polyA enriched RNA was isolated by mTRAP™ Total Kit (Active Motif, Carlsbad, Calif., USA). Double stranded cDNA from each day was synthesized with a SMART cDNA library Construct Kit (Takara Bio Inc., Otsu, Shiga, Japan). The cDNA was cleaved with Sfi I and the cDNA was size fractionated by 0.8% agarose gel electrophoresis using 44 mM Tris base, 44 mM boric acid, 0.5 mM EDTA buffer. The fraction of cDNA of 500 bp and larger was excised from the gel and purified using a GFX® PCR DNA and Gel Band Purification Kit (GE Healthcare, Piscataway, N.J., USA) according to the manufacturer's instructions. Then equal amounts of cDNA from each day were pooled for library construction.

The prepared cDNA was then directionally cloned by ligation into Sfi I cleaved pMHas7 (WO 2009/037253) using T4 ligase (New England Biolabs, Inc., Beverly, Mass., USA) according to the manufacturer's instructions. The ligation mixture was electroporated into *E. coli* ELECTROMAX™ DH10B™ cells (Invitrogen Corporation, Carlsbad, Calif., USA) using a GENE PULSER® and Pulse Controller (Bio-Rad Laboratories, Inc., Hercules, Calif., USA) at 25 µF, 25 mAmp, 1.8 kV with a 1 mm gap cuvette according to the manufacturer's procedure.

The electroporated cells were plated onto LB plates supplemented with 50 mg of kanamycin per liter. A cDNA plasmid pool was prepared from 100,000 total transformants of the original pMHas7 vector ligation. Plasmid DNA was prepared directly from the pool of colonies using a Plasmid Kit (QIAGEN GmbH, Hilden, Germany).

The method of transposon assisted signal trapping is described in WO 2001/77315. The TAST plasmid pool was sequenced by SinoGenoMax Company Limited (Beijing, China). The open reading frame of the *Malbranchea cinnamomea* strain NN051564 GH10 xylanase was identified from the cDNA sequence released by the SinoGenoMax. The cDNA sequence of *Malbranchea cinnamomea* GH10 xylanase was identified by performing a TFasty search against several known GH10 xylanase protein sequences as queries. Tfasty compares a protein sequence to a DNA sequence database, calculating similarities with frameshifts to the forward and reverse orientations, and allowing frameshifts within codons. Tfasty is part of the FASTA3 program suite (Pearson et al., 2000, *Methods Mol. Biol.* 132:185-219). The identified cDNA sequence is listed as SEQ ID NO: 21.

Example 3

Genome Sequencing, Assembly and Annotation of *Scytalidium Thermophilum* strain NN047338, *Malbranchea cinnamomea* Strain NN044758, *Corynascus thermophilus* Strain NN000308 and *Penicillium oxalicum* Strain NN051380

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using the SOAPdenovo program (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The GH10 xylanases were identified directly by analysis of the Blast results. The Agene program (Munch and Krogh, 2006, *BMC Bioinformatics* 7: 263) and SignalP program (Nielsen et al., 1997, *Protein Engineering* 10:1-6) were used to identify starting codons. The SignalP program was further used to predict the signal peptide. Pepstats (Rice et al., 2000, *Trends Genet.* 16(6): 276-277) was used to predict the isoelectric points and molecular weights of the deduced amino acid sequences.

Example 4

Cloning of *Scytalidium thermophilum* Strain NN047338 GH10 Xylanase Coding Sequences from Genomic DNA Four *Scytalidium thermophilum* strain NN047338 GH10 xylanase coding sequences shown below in Table 1 were selected for cloning.

TABLE 1

| GH10 xylanase genes | | |
|---|---|---|
| Gene name | DNA sequence | Protein sequence |
| GH10_ZY577198_20 | SEQ ID NO: 1 | SEQ ID NO: 2 |
| GH10_ZY577319_22 | SEQ ID NO: 3 | SEQ ID NO: 4 |
| GH10_ZY577226_23 | SEQ ID NO: 5 | SEQ ID NO: 6 |
| GH10_ZY577198_133 | SEQ ID NO: 7 | SEQ ID NO: 8 |

Based on the DNA information (SEQ ID NOs: 1, 3, 5, and 7) obtained from genome sequencing, oligonucleotide primers shown below were designed to amplify the four GH10 xylanase coding sequences from the genomic DNA of *Scytalidium thermophilum* NN047338. The primers were synthesized by Invitrogen, Beijing, China.

SEQ ID 1_forward:
(SEQ ID NO: 22)
ACACAACTGGGGATCCACCatggcgaggctc

SEQ ID 1_reverse:
(SEQ ID NO: 23)
GTCACCCTCTAGATCTcgaccccaaagaaatgggta

SEQ ID 3_forward:
(SEQ ID NO: 24)
ACACAACTGGGGATCCACCatgcgtttctccgcc

SEQ ID 3_reverse:
(SEQ ID NO: 25)
GTCACCCTCTAGATCTaaattgcggtcacagagtccag

SEQ ID 5_forward:
(SEQ ID NO: 26)
ACACAACTGGGGATCCACCatgcatctcgcttcgtcgc

SEQ ID 5_reverse:
(SEQ ID NO: 27)
GTCACCCTCTAGATCTaagtctccacccgcatcgac

SEQ ID 7_forward:
(SEQ ID NO: 28)
ACACAACTGGGGATCCACCatgagagctccgtc

SEQ ID 7_reverse:
(SEQ ID NO: 29)
GTCACCCTCTAGATCT gacaaatcttcacacagcccaatg

Lowercase characters represent the coding regions of the genes in forward primers and the flanking region of the gene in reverse primers, while capitalized parts were homologous to the insertion sites of pPFJO355 vector which has been described in WO2011005867.

For each gene, 20 picomoles of each primer pair (forward and reverse primers) were used in a PCR reaction composed of 2 μl of *Scytalidium thermophilum* NN047338 genomic DNA, 10 μl of 5×GC Buffer (Finnzymes Oy, Espoo, Finland), 1.5 μl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl. The amplification was performed using a Peltier Thermal Cycler (MJ Research Inc., South San Francisco, Calif., USA) programmed for denaturing at 98° C. for 1 minute; 6 cycles of denaturing at 98° C. for 15 seconds, annealing at 63° C. for 30 seconds, with a 1° C. decrease per cycle and elongation at 72° C. for 100 seconds; 23 cycles each at 98° C. for 15 seconds, 62° C. for 30 seconds and 72° C. for 100 seconds; and a final extension at 72° C. for 7 minutes. The heat block then went to a 4° C. soak cycle.

The PCR products were isolated by 1.0% agarose gel electrophoresis using 90 mM Tris-borate and 1 mM EDTA (TBE) buffer where product bands as shown in Table 2 from each PCR reaction were observed. The PCR products were then purified from solution using an ILLUSTRA™ GFX™ PCR DNA and Gel Band Purification Kit (GE Healthcare, Buckinghamshire, UK) according to the manufacturer's instructions.

TABLE 2

| Size of PCR product | |
|---|---|
| Gene name | Size of PCR product |
| GH10_ZY577198_20 | 1.4 kb |
| GH10_ZY577319_22 | 1.4 kb |

TABLE 2-continued

| Size of PCR product | |
|---|---|
| Gene name | Size of PCR product |
| GH10_ZY577226_23 | 1.2 kb |
| GH10_ZY577198_133 | 1.1 kb |

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions.

TABLE 3

Figure 2:
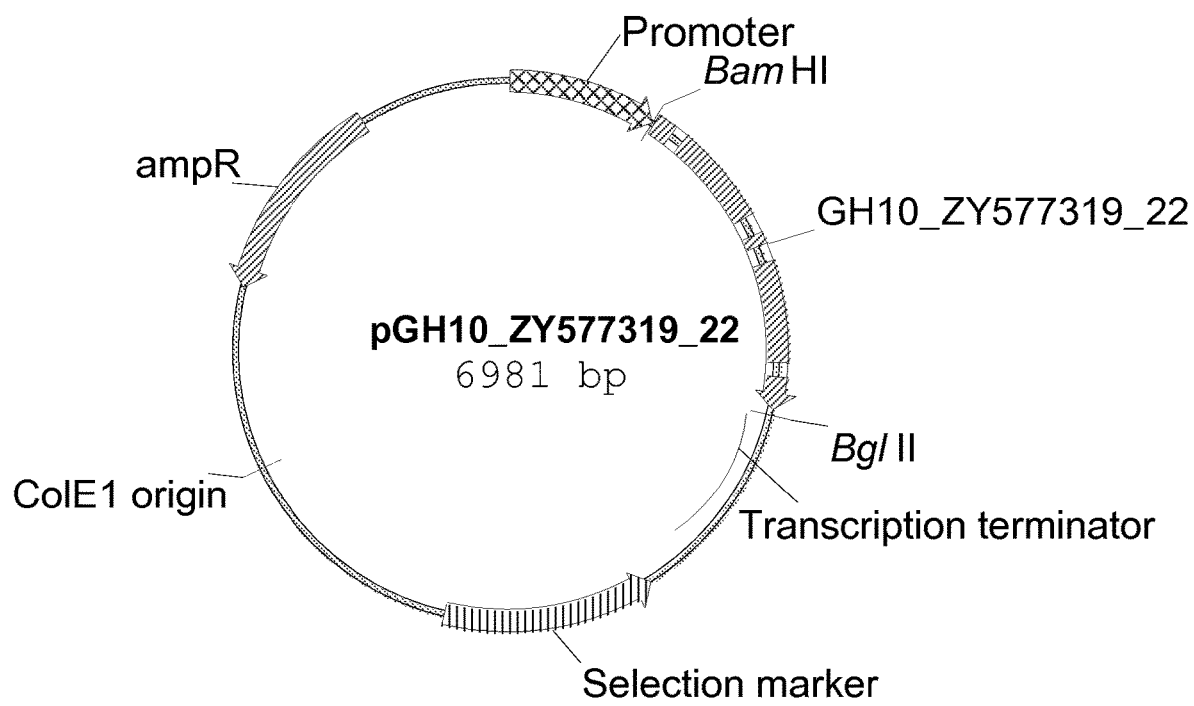
FIG. 2 shows a restriction map of plasmid pGH10_ZY577319_22.
Figure 3:
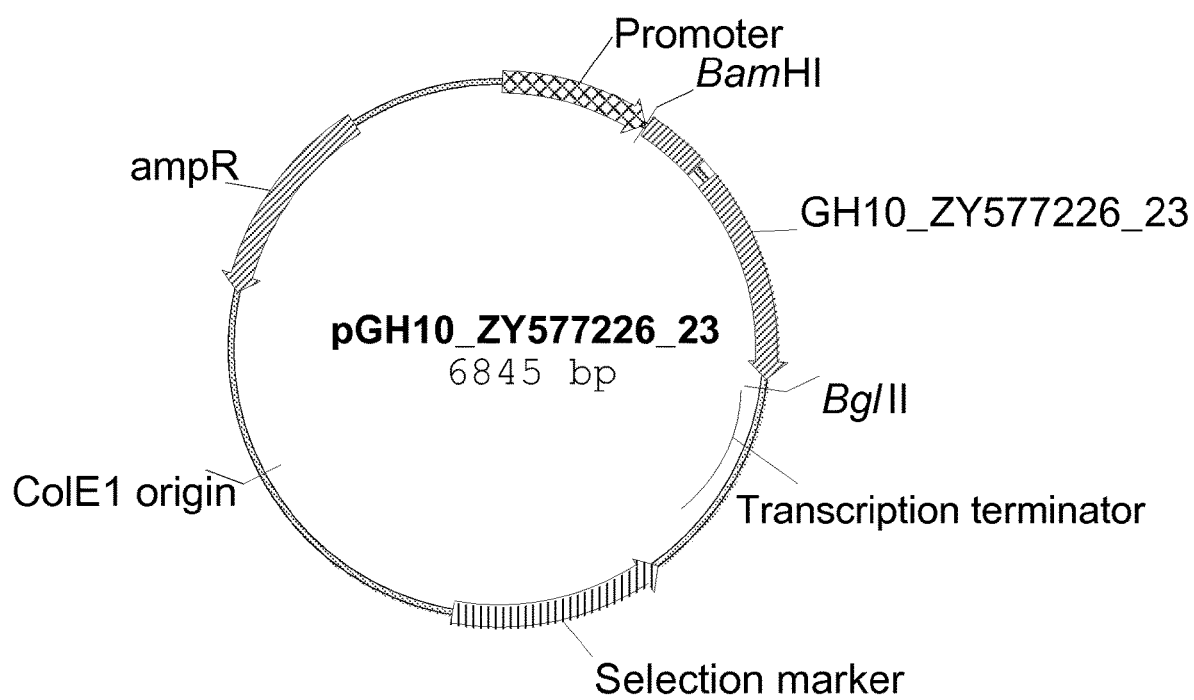
FIG. 3 shows a restriction map of plasmid pGH10_ZY577226_23.
Figure 4:
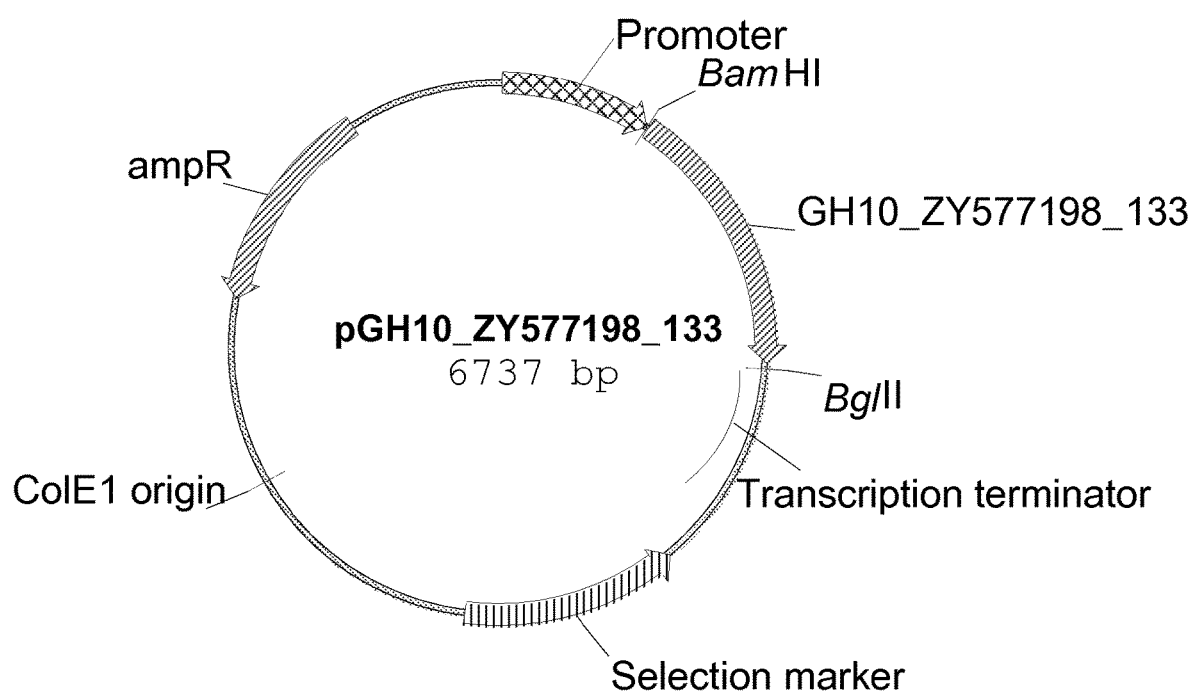
FIG. 4 shows a restriction map of plasmid pGH10_ZY577198_133.

| Plasmids | | |
|---|---|---|
| Gene name | Plasmid | DNA map |
| GH10_ZY577198_20 | pGH10_ZY577198_20 | FIG. 1 |
| GH10_ZY577319_22 | pGH10_ZY577319_22 | FIG. 2 |
| GH10_ZY577226_23 | pGH10_ZY577226_23 | FIG. 3 |
| GH10_ZY577198_133 | pGH10_ZY577198_133 | FIG. 4 |

The PCR products and the digested vector were ligated together using an IN-FUSION® CF Dry-down PCR Cloning Kit (Clontech Laboratories, Inc., Mountain View, Calif., USA) resulting in plasmids (Table 3) pGH10_ZY577198_20 (FIG. 1), pGH10_ZY577319_22 (FIG. 2), pGH10_ZY577226_23 (FIG. 3), and pGH10_ZY577198_133 (FIG. 4), in which transcription of the *Scytalidium thermophilum* GH10 xylanase coding sequences was under the control of an *Aspergillus oryzae* alpha-amylase gene promoter. For each ligation reaction, 30 ng of pPFJO355, digested with Bam HI and Bgl II, and 60 ng of each purified *Scytalidium thermophilum* GH10 xylanase PCR product were added to separate reaction vials and resuspended in a final volume of 10 µl by addition of deionized water. The reactions were incubated at 37° C. for 15 minutes and then 50° C. for 15 minutes. Three µl of each reaction were used to transform *E. coli* TOP10 competent cells (TIANGEN Biotech (Beijing) Co. Ltd., Beijing, China). *E. coli* transformants containing each expression construct were detected by colony PCR. Colony PCR is a method for quick screening of plasmid inserts directly from *E. coli* colonies. Briefly, in the premixed PCR solution aliquot in each PCR tube, including PCR buffer, $MgCl_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. Plasmid DNA was prepared from colonies showing an insert with the expected size using a QIAPREP® Spin Miniprep Kit (QIAGEN GmbH, Hilden, Germany). The *Scytalidium thermophilum* GH10 xylanase genes inserted in pGH10_ZY577198_20, pGH10_ZY577319_22, pGH10_ZY577226_23, and pGH10_ZY577198_133 were confirmed by DNA sequencing using a 3730XL DNA Analyzer (Applied Biosystems Inc., Foster City, Calif., USA).

Example 5

Cloning of a *Malbranchea cinnamomea* Strain NN051564 GH10 Xylanase Coding Sequence from Genomic DNA Based on the cDNA information (SEQ ID NO: 21) obtained from transposon assisted signal trapping, oligonucleotide primers shown below were designed to amplify a GH10 xylanase coding sequence(xyn13) from genomic DNA of *Malbranchea cinnamomea* strain NN051564. The primers were synthesized by Invitrogen, Beijing, China.

```
Forward primer:
                                   (SEQ ID NO: 30)
ACACAACTGGGGATCCACCatgcgcatatcactcgttcttc Reverse primer:
                                   (SEQ ID NO: 31)
GTCACCCTCTAGATCTctactgcaaggactgggcaacag
```

Lowercase characters represent coding regions of the genes, while capitalized characters are a region homologous to the insertion sites of plasmid pPFJO355.

Twenty picomoles of the two primers were used in a PCR reaction composed of 4 µl of *Malbranchea cinnamomea*NN051564 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase in a final volume of 50 µl. The amplification was performed using a Peltier Thermal Cycler programmed for denaturing at 94° C. for 3 minutes; 5 cycles of denaturing at 94° C. for 40 seconds, annealing at 63° C. for 40 seconds, with a 1° C. increase per cycle and elongation at 72° C. for 90 seconds; 24 cycles each at 94° C. for 40 seconds, 68° C. for 40 seconds, and 72° C. for 90 seconds; and a final extension at 72° C. for 10 minutes. The heat block then went to a 10° C. soak cycle.

Three µl of the PCR reaction were analyzed by 1.0% agarose gel electrophoresis using TBE buffer where a single band of approximately 1.6 kb was observed. The remaining PCR reaction was purified using an ILLUSTRA™ GFX™ PCR DNA and Gel Band Purification Kit.

Figure 5:
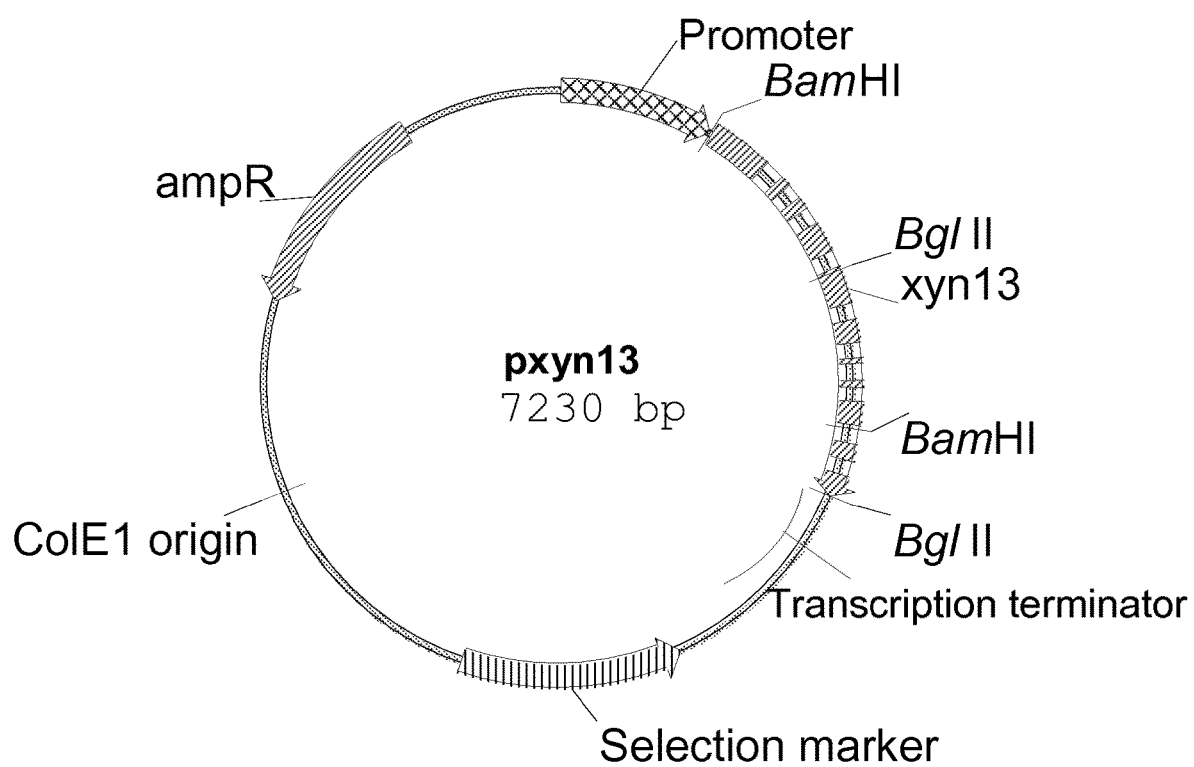
FIG. 5 shows a restriction map of plasmid pxyn13.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions. The PCR product and the digested vector were ligated together using an IN-FUSION® CF Dry-down PCR Cloning Kit resulting in plasmid pxyn13 (FIG. 5) in which transcription of the *Malbranchea cinnamomea* GH10 xylanase coding sequence was under the control of an *Aspergillus oryzae* alpha-amylase gene promoter. For the ligation reaction, 30 ng of pPFJO355, digested with Bam HI and Bgl II, and 60 ng of the purified *Malbranchea cinnamomea* GH10 xylanase PCR product were added to a reaction vial and resuspended in a final volume of 10 µl by addition of deionized water. The reaction was incubated at 37° C. for 15 minutes and then 50° C. for 15 minutes. Three µl of the reaction were used to transform *E. coli* TOP10 competent cells. *E. coli* transformants containing the expression construct were detected by colony PCR as described in Example 4 and plasmid DNA was prepared using a QIAPREP® Spin Miniprep Kit. The *Malbranchea cinnamomea* GH10 xylanase gene inserted in pxyn13 was confirmed by DNA sequencing using a 3730XL DNA Analyzer. The genomic DNA sequence and the deduced amino acid sequence of *Malbranchea cinnamomea* GH10 xylanase coding sequence are shown as SEQ ID NOs: 9 and 10, respectively.

Example 6

Cloning of a *Malbranchea cinnamomea* Strain NN044758 GH10 Xylanase Coding Sequence from Genomic DNA Based on the DNA information obtained from genome sequencing of the *Malbranchea cinnamomea* strain NN044758, oligonucleotide primers shown below were designed to amplify aGH10 xylanase coding sequence, GH10_ZY582331_279, from genomic DNA of *Malbranchea cinnamomea* NN044758. Primers were synthesized by Invitrogen, Beijing, China.

```
Forward primer:
                                       (SEQ ID NO: 32)
ACACAACTGGGGATCCACCatggtgaagctactcccagtcatcg Reverse primer:
                                       (SEQ ID NO: 33)
GTCACCCTCTAGATCTcgccaacagatcctaatgggac
```

Lowercase characters represent the coding regions of the genes in forward primers and the flanking region of the gene in reverse primers, while capitalized parts were homologous to the insertion sites of pPFJO355 vector.

Twenty picomoles of each of the forward and reverse primers were used in a PCR reaction composed of 2 μl of *Malbranchea cinnamomea* NN044758 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplification was performed using a Peltier Thermal Cycler programmed for denaturing at 94° C. for 1 minutes; 6 cycles of denaturing at 94° C. for 15 seconds, annealing at 68° C. for 30 seconds, with a 1° C. decrease per cycle and elongation at 72° C. for 100 seconds; 23 cycles each at 94° C. for 15 seconds, 63° C. for 30 seconds and 72° C. for 100 seconds; and a final extension at 72° C. for 5 minutes. The heat block then went to a 4° C. soak cycle.

The PCR product was isolated by 1.0% agarose gel electrophoresis using TBE buffer where a single product band of 1.4 kb was observed. The PCR product was then purified from solution using an ILLUSTRA™ GFX™ PCR DNA and Gel Band Purification Kit according to the manufacturer's instructions.

Figure 6:
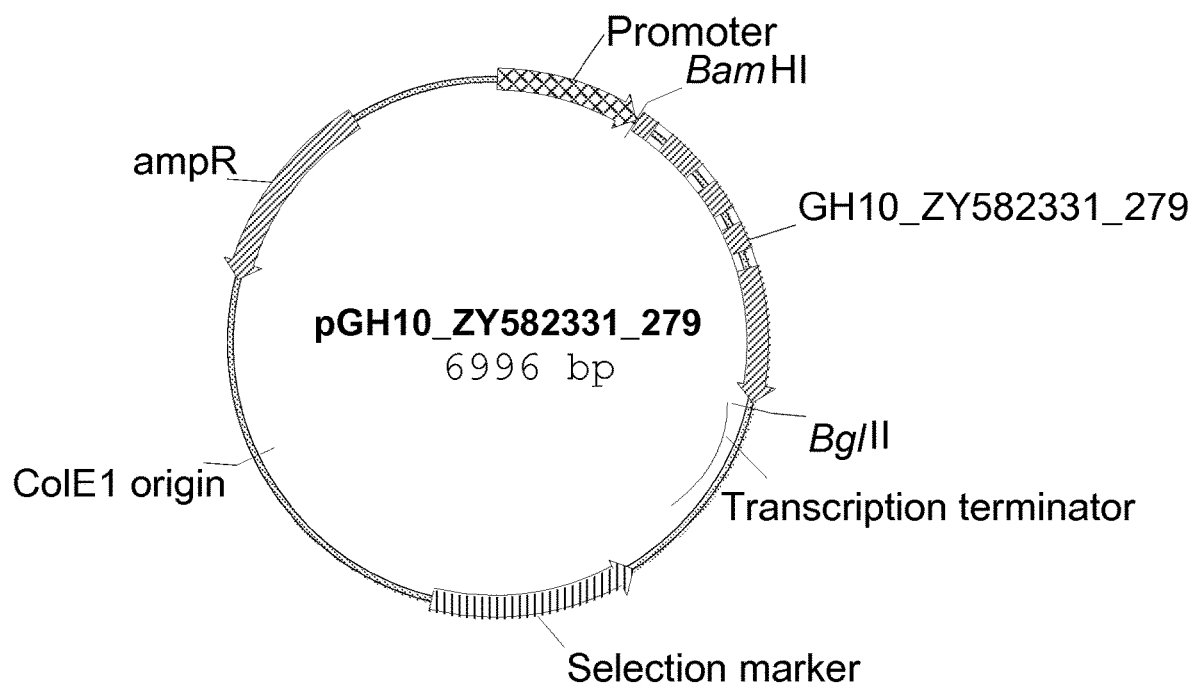
FIG. 6 shows a restriction map of plasmid pGH10_ZY582331_279.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions. An IN-FUSION® CF Dry-down Cloning Kit was used to clone the fragment directly into the expression vector pPFJO355, without the need for restriction digestion and ligation. The PCR product and the digested vector were ligated together using an IN-FUSION® CF Dry-down PCR Cloning Kit resulting in plasmidpGH10-ZY582331_279 (FIG. 6), in which transcription of the *Malbranchea cinnamomea* GH10 xylanase coding sequence was under the control of an *Aspergillus oryzae* alpha-amylase gene promoter. For the ligation reaction, 30 ng of pPFJO355, digested with Bam HI and Bgl II, and 60 ng of the purified *Malbranchea cinnamomea* GH10 xylanase PCR product were added to a reaction vial and resuspended in a final volume of 10 μl by addition of deionized water. The reaction was incubated at 37° C. for 15 minutes and then 50° C. for 15 minutes. Three μl of the reaction were used to transform *E. coli* TOP10 competent cells. *E. coli* transformants containing the expression construct were detected by colony PCR as described in Example 4 and plasmid DNA was prepared using a QIAPREP® Spin Miniprep Kit. The *Malbranchea cinnamomea* GH10 xylanase coding sequence inserted in pGH10_ZY582331_279 was confirmed by DNA sequencing using a 3730XL DNA Analyzer.

The genomic DNA sequence and the deduced amino acid sequence are shown as SEQ ID NO: 11 and SEQ ID NO: 12, respectively.

Example 7

Cloning of *Corynascus thermophilus* CBS 174.70 GH10 Xylanase Coding Sequences from Genomic DNA Three GH10 xylanase genes from *Corynascus thermophilus* strain CBS 174.70 shown below in Table 4 were selected for cloning.

TABLE 4

| GH10 xylanase genes | | |
|---|---|---|
| Gene name | DNA sequence | Protein sequence |
| GH10_Mf4036 | SEQ ID NO: 13 | SEQ ID NO: 14 |
| GH10_Mf2809 | SEQ ID NO: 15 | SEQ ID NO: 16 |
| GH10_Mf0530 | SEQ ID NO: 17 | SEQ ID NO: 18 |

Based on the DNA information obtained from genome sequencing of *Corynascus thermophilus* strain CBS 174.70, oligonucleotide primers shown below were designed to amplify the GH10 xylanase coding sequences from genomic DNA of the *Corynascus thermophilus* strain CBS 174.70. The primers were synthesized by Invitrogen, Beijing, China.

```
SEQ ID 14_forward:
                                       (SEQ ID NO: 34)
ACACAACTGGGGATCCACCatgcggttttctgcgcctc SEQ ID 14_reverse:
                                       (SEQ ID NO: 35)
GTCACCCTCTAGATCTaccgtccaccgttcctcttagag SEQ ID 16_forward:
                                       (SEQ ID NO: 36)
ACACAACTGGGGATCCACCatgcgactctccgcg SEQ ID 16_reverse:
                                       (SEQ ID NO: 37)
GTCACCCTCTAGATCTcacaggttgggggatgag SEQ ID 18_forward:
                                       (SEQ ID NO: 38)
ACACAACTGGGGATCCACCatgcgtactctcgccttcg SEQ ID 18_reverse:
                                       (SEQ ID NO: 39)
GTCACCCTCTAGATCTacccatccatcacaatcacac
```

Lowercase characters represent the coding regions of the genes in forward primers and the flanking region of the gene in reverse primers, while capitalized parts were homologous to the insertion sites of pPFJO355 vector.

For each gene, 20 picomoles of each primer pair (forward and reverse primers) were used in a PCR reaction composed of 2 μl of *Corynascus thermophilus* NN000308 genomic DNA, 10 μl of 5×HF/GC Buffer (Finnzymes Oy, Espoo, Finland), 1.5 μl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl.

The amplification of GH10_Mf0530 was performed using a Peltier Thermal Cycler programmed for denaturing at 98° C. for 1 minute; 10 cycles of denaturing at 98° C. for 15 seconds, annealing at 70° C. for 30 seconds, with a 1° C. decrease per cycle and elongation at 72° C. for 90 seconds;

20 cycles each at 94° C. for 30 seconds, 60° C. for 30 seconds, and 72° C. for 90 seconds; and a final extension at 72° C. for 5 minutes. The heat block then went to a 4° C. soak cycle.

The amplification of GH10_Mf4036 and GH10_Mf2809 was performed using a Peltier Thermal Cycler programmed for denaturing at 98° C. for 1 minute; 7 cycles of denaturing at 98° C. for 30 seconds, annealing at 65° C. for 30 seconds, with a 1° C. decrease per cycle and elongation at 72° C. for 2 minutes; 25 cycles each at 94° C. for 30 seconds, 60° C. for 30 seconds, and 72° C. for 2 minutes; and a final extension at 72° C. for 5 minutes. The heat block then went to a 4° C. soak cycle.

The PCR products were isolated by 1.0% agarose gel electrophoresis using TBE buffer where product bands as shown in Table 5 from each PCR reaction were observed. The PCR products were then purified from solution using an ILLUSTRA™ GFX™ PCR DNA and Gel Band Purification Kit according to the manufacturer's instructions. GH10_Mf4036 and GH10_Mf5030 each showed a PCR product at approximately 1.4 kb, while GH10_Mf2809 showed a PCR product at approximately 1.5 kb.

TABLE 5

| Size of PCR product | |
|---|---|
| Gene name | Size of PCR product |
| GH10_Mf4036 | ~1.4 kb |
| GH10_Mf2809 | ~1.5 kb |
| GH10_Mf0530 | ~1.4 kb |

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions.

TABLE 6

Figure 7:
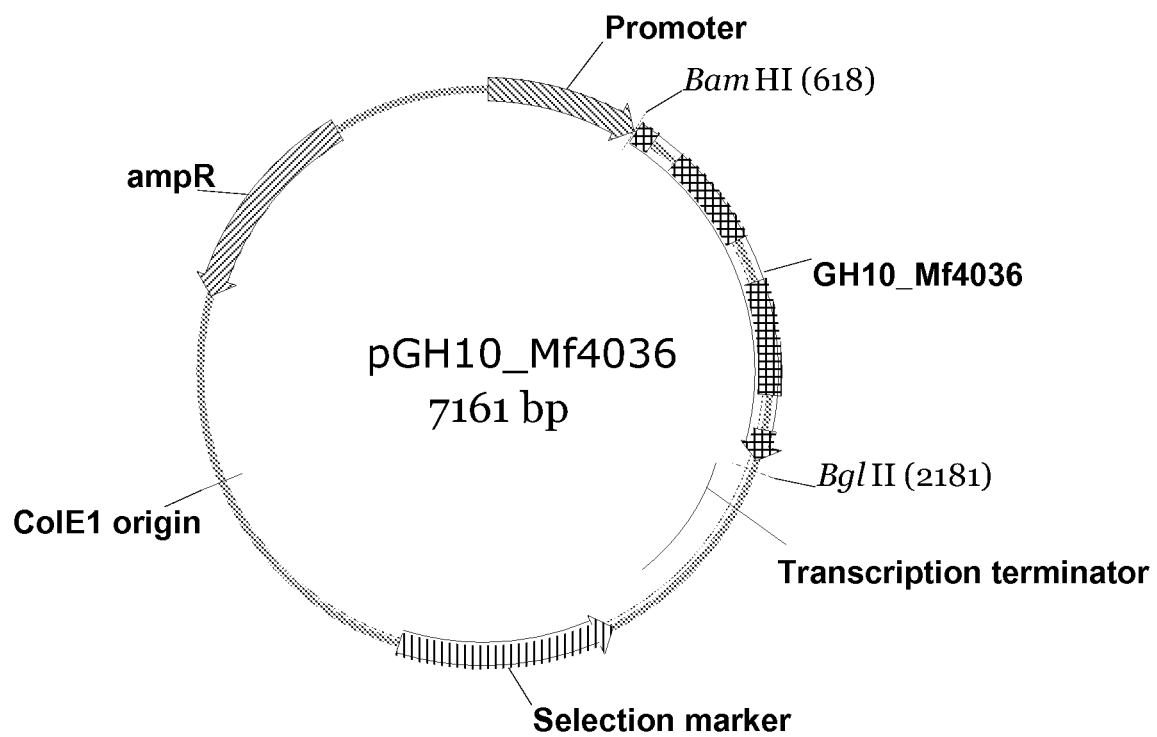
FIG. 7 shows a restriction map of plasmid pGH10_Mf4036.
Figure 8:
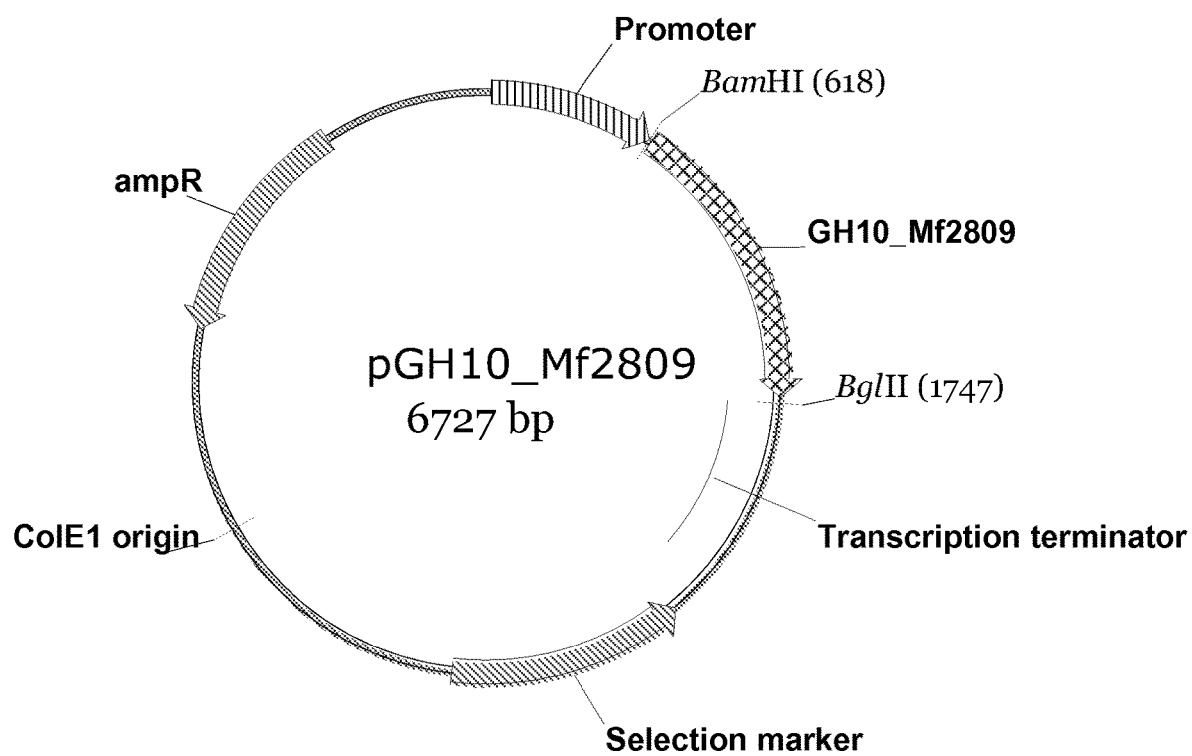
FIG. 8 shows a restriction map of plasmid pGH10_Mf2809.
Figure 9:
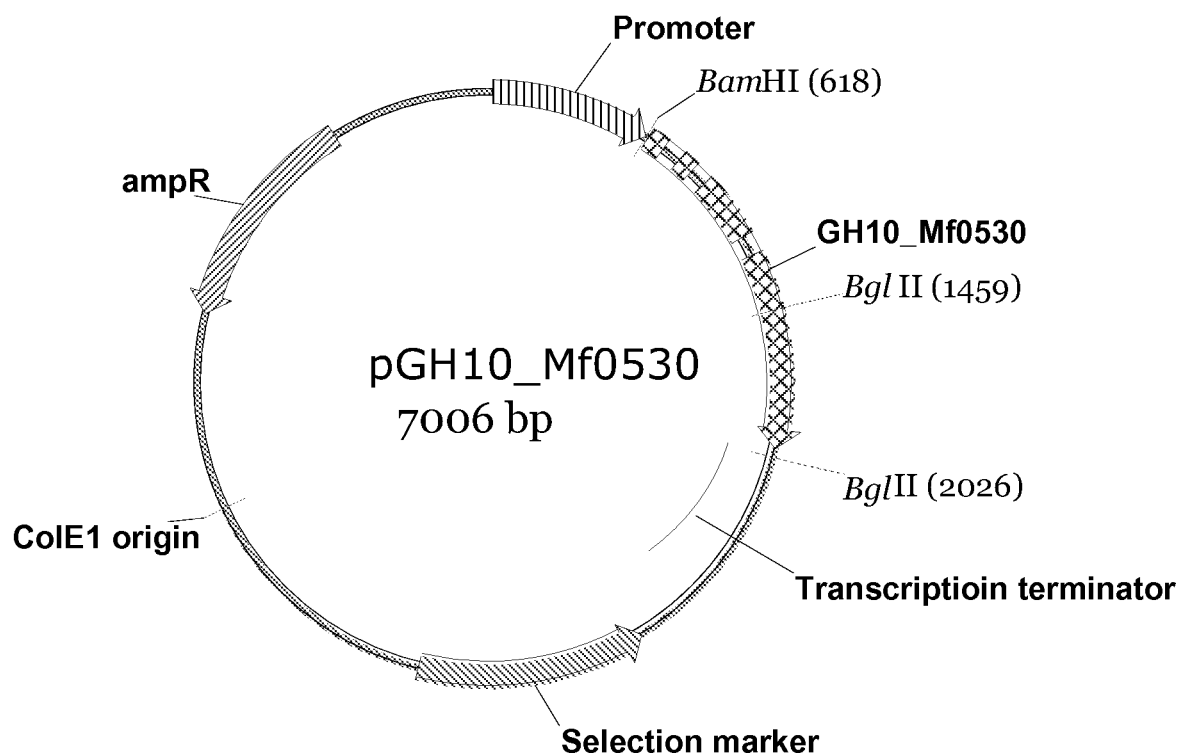
FIG. 9 shows a restriction map of plasmid pGH10_Mf0530.

| Plasmids | | |
|---|---|---|
| Gene name | Plasmid | DNA map |
| GH10_Mf4036 | pGH10_Mf4036 | FIG. 7 |
| GH10_Mf2809 | pGH10_Mf2809 | FIG. 8 |
| GH10_Mf0530 | pGH10_Mf0530 | FIG. 9 |

The PCR products and the digested vector were ligated together using an IN-FUSION® CF Dry-down PCR Cloning Kit resulting in plasmids (Table 6) pGH10_Mf4036 (FIG. 7), pGH10_Mf2809 (FIG. 8), and pGH10_Mf0530 (FIG. 9) in which the transcription of the *Corynascus thermophilus* GH10 xylanase coding sequences was under the control of an *Aspergillus oryzae* alpha-amylase gene promoter. Briefly, for each ligation reaction, 30 ng of pPFJO355, digested with Bam HI and Bgl II, and 60 ng of each purified *Corynascus thermophilus* GH10 xylanase PCR product were added to separate reaction vials and resuspended in a final volume of 10 μl by addition of deionized water. The reactions were incubated at 37° C. for 15 minutes and then 50° C. for 15 minutes. Three μl of each reaction were used to transform *E. coli* TOP10 competent cells (TIANGEN Biotech (Beijing) Co. Ltd., Beijing, China). *E. coli* transformants containing each expression construct were detected by colony PCR as described in Example 4. The plasmid DNA was prepared using a QIAPREP® Spin Miniprep Kit. The *Corynascus thermophilus* GH10 xylanase genes inserted in pGH10_Mf4036, pGH10_Mf2809, and pGH10_Mf0530 were confirmed by DNA sequencing using a 3730XL DNA Analyzer (Applied Biosystems Inc, Foster City, Calif., USA).

Example 8

Cloning of a *Penicillium Oxalicum* Strain NN051380 GH10 Xylanase Coding Sequence from Genomic DNA Based on the gene information obtained by genome sequencing of *Penicillium oxalicum* strain NN051380, oligonucleotide primers shown below were designed to amplify a GH10 xylanase coding sequence, GH10_ZY569164_676, from the genomic DNA of the *Penicillium oxalicum* strain NN051380.

```
Forward primer:
                              (SEQ ID NO: 40)
ACACAACTGGGGATCCACCatgcgctccacgttcatgg Reverse primer:
                              (SEQ ID NO: 41)
GTCACCCTCTAGATCTgaagcatcctctagtgaggcctatcaa
```

Lowercase characters represent the coding regions of the genes in forward primers and the flanking region of the gene in reverse primers, while capitalized parts were homologous to the insertion sites of pPFJO355 vector.

An IN-FUSION® CF Dry-down Cloning Kit was used to clone the fragment directly into the expression vector pPFJO355, without the need for restriction digestion and ligation.

Twenty picomoles of each of the primers above were used in a PCR reaction composed of 2 μl of *Penicillium oxalicum* genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplification was performed using a Peltier Thermal Cycler programmed for denaturing at 98° C. for 1 minute; 6 cycles of denaturing at 98° C. for 15 seconds, annealing at 65° C. for 30 seconds, with a 1° C. decrease per cycle and elongation at 72° C. for 70 seconds; 25 cycles each at 98° C. for 15 seconds, 62° C. for 30 seconds, and 72° C. for 70 seconds; and a final extension at 72° C. for 5 minutes. The heat block then went to a 4° C. soak cycle.

The reaction products were isolated by 1.0% agarose gel electrophoresis using TBE buffer where an approximately 1.2 kb product band was excised from the gel, and purified using an ILLUSTRA™ GFX™ PCR DNA and Gel Band Purification Kit according to the manufacturer's instructions.

Figure 10:
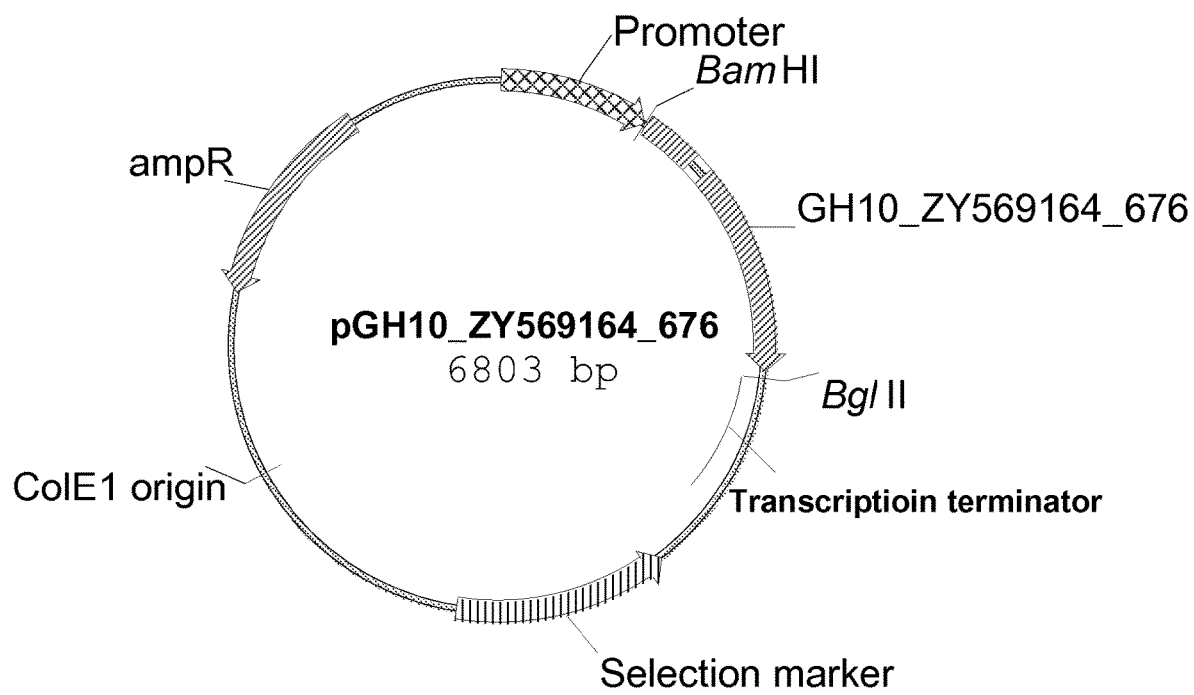
FIG. 10 shows a restriction map of plasmid pGH10_ZY569164_676.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions. The PCR product and the digested vector were ligated together using an IN-FUSION® CF Dry-down PCR Cloning Kit resulting in pGH10_ZY569164_676 (FIG. 10) in which transcription of the *Penicillium oxalicum* GH10 xylanase coding sequence was under the control of an *Aspergillus oryzae* alpha-amylase gene promoter. For the ligation reaction, 30 ng of pPFJO355, digested with Bam HI and Bgl II, and 60 ng of the *Penicillium oxalicum* GH10 xylanase purified PCR product were added to a reaction vial and resuspended in a final volume of 10 µl by addition of deionized water. The reaction was incubated at 37° C. for 15 minutes and then 50° C. for 15 minutes. Three µl of the reaction were used to transform *E. coli* TOP10 competent cells. An *E. coli* transformant containing pGH10_ZY569164_676 was detected by colony PCR as described in Example 4 and plasmid DNA was prepared using a QIAPREP® Spin Miniprep Kit. The *Penicillium oxalicum* GH10 xylanase gene inserted in pGH10_ZY569164_676 was confirmed by DNA sequencing using a 3730XL DNA Analyzer.

The genomic DNA sequence and the deduced amino acid sequence are shown as SEQ ID NO: 19 and SEQ ID NO: 20, respectively.

Example 9

Characterization of the Genomic DNAs Encoding GH10 Xylanases

The genomic DNA sequence and deduced amino acid sequence of a *Scytalidium thermophilum* GH10 xylanase coding sequence are shown in SEQ ID NO: 1 (D822JR) and SEQ ID NO: 2(P244XT), respectively. The coding sequence is 1314 bp including the stop codon, which is interrupted by one intron of 89 bp (nucleotides 374 to 462). The encoded predicted protein is 406 amino acids. Using the SignalP program (Nielsen et al., 1997, *Protein Engineering* 10:1-6), a signal peptide of 20 residues was predicted. The predicted mature protein contains 386 amino acids with a predicted molecular mass of 42.38 kDa and a predicted isoelectric point of 4.61.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Scytalidium thermophilum* genomic DNA encoding a GH10 xylanase shares 54.62% identity (excluding gaps) to the deduced amino acid sequence of a GH10 xylanase from *Colletotrichum graminicola* (UNIPROT E3Q8L2).

The genomic DNA sequence and deduced amino acid sequence of a *Scytalidium thermophilum* GH10 xylanase coding sequence are shown in SEQ ID NO: 3 (D822JT) and SEQ ID NO: 4(P244XW), respectively. The coding sequence is 1350 bp including the stop codon, which is interrupted by four introns of 54 bp (nucleotides 84 to 137), 80 bp (nucleotides 542 to 621), 75 bp (nucleotides 669 to 743), and 58 bp (nucleotides 1158 to 1215). The encoded predicted protein is 360 amino acids. Using the SignalP program (Nielsen et al., 1997, supra), a signal peptide of 17 residues was predicted. The predicted mature protein contains 343 amino acids with a predicted molecular mass of 38.93 kDa and a predicted isoelectric point of 7.17.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Scytalidium thermophilum* genomic DNA encoding a GH10 xylanase shares 68.28% identity (excluding gaps) to the deduced amino acid sequence of a GH10 xylanase from *Phaeosphaeria nodorum* (UNIPROT B6DQK8).

The genomic DNA sequence and deduced amino acid sequence of a *Scytalidium thermophilum* GH10 xylanase coding sequence are shown in SEQ ID NO: 5 (D822JW) and SEQ ID NO: 6(P244Y1), respectively. The coding sequence is 1199 bp including the stop codon, which is interrupted by one intron of 68 bp (nucleotides 265 to 332). The encoded predicted protein is 376 amino acids. Using the SignalP program (Nielsen et al., 1997, supra), a signal peptide of 18 residues was predicted. The predicted mature protein contains 358 amino acids with a predicted molecular mass of 40.29 kDa and a predicted isoelectric point of 6.30.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Scytalidium thermophilum* genomic DNA encoding a GH10 xylanase shares 78.59% identity (excluding gaps) to the deduced amino acid sequence of a GH10 xylanase from *Corynascus heterothallicus* (GENESEQP AEB00303).

The genomic DNA sequence and deduced amino acid sequence of a *Scytalidium thermophilum* GH10 xylanase coding sequence are shown in SEQ ID NO: 7 (D822JX) and SEQ ID NO: 8(P244Y2), respectively. The coding sequence is 1104 bp including the stop codon without any introns. The encoded predicted protein is 367 amino acids. Using the SignalP program (Nielsen et al., 1997, supra), a signal peptide of 22 residues was predicted. The predicted mature protein contains 345 amino acids with a predicted molecular mass of 39.03 kDa and a predicted isoelectric point of 5.42.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Scytalidium thermophilum* genomic DNA encoding a GH10 xylanase shares 77.98% identity (excluding gaps) to the deduced amino acid sequence of a GH10 xylanase from *Podospora anserine* (UNIPROT B2B789).

The genomic DNA sequence and deduced amino acid sequence of a *Malbranchea cinnamomea* GH10 xylanase coding sequence are shown in SEQ ID NO: 9 (D6RM) and SEQ ID NO: 10(P23DM4), respectively. The coding sequence is 1623 bp including the stop codon, which is interrupted by ten introns of 76 bp (nucleotides 239 to 314), 59 bp (nucleotides 356 to 414), 68 bp (nucleotides 464 to 531), 63 bp (nucleotides 654 to 716), 62 bp (nucleotides 863 to 925), 60 bp (nucleotides 1015 to 1074), 68 bp (nucleotides 1094 to 1161), 56 bp (nucleotides 1189 to 1244), 73 bp (nucleotides 1334 to 1406), and 58 bp (nucleotides 1473 to 1530). The encoded predicted protein is 326 amino acids. Using the SignalP program (Nielsen et al., 1997, supra), a signal peptide of 18 residues was predicted. The predicted mature protein contains 308 amino acids with a predicted molecular mass of 33.52 kDa and a predicted isoelectric point of 4.89.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Malbranchea cinnamomea* genomic DNA encoding a GH10 xylanase shares 66.88% identity (excluding gaps) to the deduced amino acid sequence of a GH10 xylanase from *Colletotrichum graminicola* (UNIPROT E3QSE3).

The genomic DNA sequence and deduced amino acid sequence of a *Malbranchea cinnamomea* GH10 xylanase coding sequence are shown in SEQ ID NO: 11 (D82 DB2) and SEQ ID NO: 12(P249XY), respectively. The coding sequence is 1365 bp including the stop codon, which is interrupted by four introns of 72 bp (nucleotides 78 to 149), 84 bp (nucleotides 319 to 402), 66 bp (nucleotides 536 to 601), and 78 bp (nucleotides 716 to 793). The encoded predicted protein is 354 amino acids. Using the SignalP program (Nielsen et al., 1997, supra), a signal peptide of 20 residues was predicted. The predicted mature protein contains 334 amino acids with a predicted molecular mass of 38.70 kDa and a predicted isoelectric point of 6.17.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Malbranchea cinnamomea* genomic DNA encoding a GH10 xylanase shares 61.56% identity (excluding gaps) to the deduced amino acid sequence of a GH10 xylanase from *Aspergillus fumigatus* (GENESEQP AZ124748).

The genomic DNA sequence and deduced amino acid sequence of a *Corynascus thermophilus* GH10 xylanase coding sequence are shown in SEQ ID NO: 13 (D1316T) and SEQ ID NO: 14 (P24MCW), respectively. The coding sequence is 1513 bp including the stop codon, which is interrupted by three introns of 120 bp (nucleotides 81 to 200), 182 bp (nucleotides 602 to 783), and 143 bp (nucleotides 1245 to 1387). The encoded predicted protein is 355 amino acids. Using the SignalP program (Nielsen et al., 1997, supra), a signal peptide of 17 residues was predicted. The predicted mature protein contains 338 amino acids with a predicted molecular mass of 37.98 kDa and a predicted isoelectric point of 5.08.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH10 xylanase shares 70.25% identity (excluding gaps) to the deduced amino acid sequence of a GH10 xylanase from *Phaeosphaeria nodorum* (UNIPROT B6DQK8).

The genomic DNA sequence and deduced amino acid sequence of a *Corynascus thermophilus* GH10 xylanase coding sequence are shown in SEQ ID NO: 15 (D1315U) and SEQ ID NO: 16 (P24MCX), respectively. The coding sequence is 1101 bp including the stop codon without any introns. The encoded predicted protein is 366 amino acids. Using the SignalP program (Nielsen et al., 1997, supra), a signal peptide of 19 residues was predicted. The predicted mature protein contains 347 amino acids with a predicted molecular mass of 39.58 kDa and a predicted isoelectric point of 7.77.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH10 xylanase shares 74.93% identity (excluding gaps) to the deduced amino acid sequence of a GH10 xylanase from *Podospora anserina* (UNIPROT B2B789).

The genomic DNA sequence and deduced amino acid sequence of a *Corynascus thermophilus* GH10 xylanase coding sequence are shown in SEQ ID NO: 17 (D82PQC) and SEQ ID NO: 18(P24FVF), respectively. The coding sequence is 1365 bp including the stop codon, which is interrupted by three introns of 74 bp (nucleotides 74 to 147), 67 bp (nucleotides 212 to 278), and 78 bp (nucleotides 530 to 607). The encoded predicted protein is 381 amino acids. Using the SignalP program (Nielsen et al., 1997, supra), a signal peptide of 17 residues was predicted. The predicted mature protein contains 364 amino acids with a predicted molecular mass of 39.42 kDa and a predicted isoelectric point of 6.37.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH10 xylanase shares 86.98% identity (excluding gaps) to the deduced amino acid sequence of a GH10 xylanase from *Chrysosporium* sp. (GENESEQP ABB05060).

The genomic DNA sequence and deduced amino acid sequence of a *Penicillium oxalicum* GH10 xylanase coding sequence are shown in SEQ ID NO: 19 (D72UED) and SEQ ID NO: 20 (P241KU), respectively. The coding sequence is 1168 bp including the stop codon, which is interrupted by one intron of 79 bp (nucleotides 235 to 313). The encoded predicted protein is 362 amino acids. Using the SignalP program (Nielsen et al., 1997, supra), a signal peptide of 17 residues was predicted. The predicted mature protein contains 345 amino acids with a predicted molecular mass of 38.06 kDa and a predicted isoelectric point of 5.73.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium oxalicum* genomic DNA encoding a GH10 xylanase shares 82.22% identity (excluding gaps) to the deduced amino acid sequence of a GH10 xylanase from *Penicillium canescens* (UNIPROT C3VEV9).

Example 10

Expression of *Scytalidium thermophilum* GH10 Xylanase Coding Sequences

*Aspergillus oryzae* HowB101 (WO95/35385) protoplasts were prepared according to the method of Christensen et al., 1988, *Bio/Technology* 6: 1419-1422, and transformed separately with 3 µg ofpGH10_ZY577319_22, 3 µg of pGH10_ZY577226_23, and 3 µg of pGH10_ZY577198_133. The transformation yielded approximately 50 transformants for each transformation. Eight transformants from each transformation were isolated to individual Minimal medium plates.

Four transformants from each transformation were inoculated separately into 3 ml of YPM medium in a 24-well plate and incubated at 30° C. with mixing at 150 rpm. After 3 days incubation, 20 µl of supernatant from each culture were analyzed by SDS-PAGE using a NUPAGE® NOVEX® 4-12% Bis-Tris Gel with MES (Invitrogen Corporation, Carlsbad, Calif., USA) according to the manufacturer's instructions. The resulting gel was stained with INSTANT-BLUE™ (Expedeon Ltd., Babraham Cambridge, UK). The SDS-PAGE profiles of the cultures showed that the three coding sequences expressed a protein(s) as shown below in Table 7. The expression strains were designated as shown in the second column.

TABLE 7

Expression of *Scytalidium thermophilum* GH10 xylanase coding sequences

| plasmid | Expression strain | Size of recombinant protein (Kd) |
|---|---|---|
| pGH10_ZY577319_22 | O5KR9 | 40 kDa |
| pGH10_ZY577226_23 | O5KRD | Two bands at 45 kDa(strong) and 40 kDa (weak) |
| pGH10_ZY577198_133 | O5KRG | Two bands at 46 kDa and 40 kDa |

Example 11

Expression of *Malbranchea cinnamomea* NN051564 GH10 Xylanase Coding Sequence

*Aspergillus oryzae* HowB101 protoplasts were prepared according to the method of Christensen et al., 1988, supra, and transformed with 3 µg of pxyn13. The transformation yielded about 50 transformants. Eight transformants were isolated to individual Minimal medium plates.

Four transformants were inoculated separately into 3 ml of YPM medium in a 24-well plate and incubated at 30° C. with mixing at 150 rpm. After 3 days incubation, 20 µl of supernatant from each culture were analyzed by SDS-PAGE using a NUPAGE® NOVEX® 4-12% Bis-Tris Gel with MES according to the manufacturer's instructions. The resulting gel was stained with INSTANTBLUE™. SDS-PAGE profiles of the cultures showed 2 out of 4 transformants expressed a protein of approximately 34 kDa. The expression strain, transformant 4, was designated *Aspergillus oryzae* EXP02789.

Example 12

Expression of *Corynascus Thermophilus* CBS 174.70 GH10 Xylanase Coding Sequences

*Aspergillus oryzae* HowB101 protoplasts were prepared according to the method of Christensen et al., 1988, supra, and transformed with 3 µg of pGH10_Mf4036, and 3 µg of pGH10_Mf0530 separately. Each transformation yielded about 50 transformants. Eight transformants of each transformation were isolated to individual Minimal medium plates.

Four transformants from each transformation were inoculated separately into 3 ml of YPM medium in a 24-well plate and incubated at 30° C. with mixing at 150 rpm. After 3 days incubation, 20 µl of supernatant from each culture were analyzed by SDS-PAGE using a NUPAGE® NOVEX® 4-12% Bis-Tris Gel with MES according to the manufacturer's instructions. The resulting gel was stained with INSTANTBLUE™ (Expedeon Ltd., Babraham Cambridge, UK). The SDS-PAGE profiles of the cultures showed that the three coding sequences expressed a protein(s) as shown below in Table 8. The expression strains were designated as shown in the second column.

TABLE 8

Expression of *Corynascus thermophilus* CBS 174.70 GH10xylanase coding sequences

| plasmid | Expression strain | Size of recombinant protein |
|---|---|---|
| pGH10_Mf4036 | O7R3T | 42 kDa |
| pGH10_Mf0530 | O7J26 | 40 kDa |

Example 13

Expression of *Penicillium oxalicum* GH10 Xylanase Genes

*Aspergillus oryzae* HowB101 protoplasts were prepared according to the method of Christensen et al., 1988, supra, and transformed with 3 µg of pGH10_ZY569164_676. The transformation yielded approximately 50 transformants. Four transformants were isolated to individual Minimal medium plates.

The four transformants were inoculated separately into 3 ml of YPM medium in a 24-well plate and incubated at 30° C. with mixing at 150 rpm. After 3 days incubation, 20 µl of supernatant from each culture were analyzed by SDS-PAGE using a NUPAGE® NOVEX® 4-12% Bis-Tris Gel with MES according to the manufacturer's instructions. The resulting gel was stained with INSTANTBLUE™. SDS-PAGE profiles of the cultures showed that the majority of the transformants had a major band at approximately 46 kDa. The expression strain was designated *Aspergillus oryzae* O4S5C.

Example 14

Fermentation of Expression Strains

A slant of each transformant was used to inoculate 4-6 shaking flasks of 2 L containing 400 ml of YPM. The total culture volume of each expression strain was shown in table 9. The shaking flasks were then shaking at 30° C., 80 rpm for 3 days. The culture was harvested on day 3 and filtered using a 0.45 µm DURAPORE® Membrane (Millipore, Bedford, Mass., USA).

TABLE 9

Fermentation of expression strains

| Expression strain | Culture volume (ml) |
|---|---|
| O5KR9 | 2400 |
| O5KRD | 1600 |
| EXP02789 | 1600 |
| O7R3T | 3200 |
| O4S5C | 2000 |

Example 15

Purification of Recombinant GH10 Xylanases from *Aspergillus Oryzae* Strains O5KR9, O5KRD, EXP02789, O4S5C, and O7R3T A 2400 ml volume of *Aspergillus oryzae* O5KR9 supernatant was precipitated with ammonium sulfate (80% saturation), re-dissolved in 50 ml of 20 mM sodium acetate pH5.5, dialyzed against the same buffer, and filtered through a 0.45 µm filter. The final volume was 80 ml. The solution was applied to a 30 ml SP SEPHAROSE® Fast Flow column (GE Healthcare Life Sciences, Piscataway, N.J., USA) equilibrated with 20 mM sodium acetate pH 5.5 and the proteins were eluted using a linear 0-0.5 M NaCl gradient. Fractions were collected and applied to a Q SEPHAROSE® Fast Flow column (GE Healthcare Life Sciences, Piscataway, N.J., USA). equilibrated with 20 mM sodium acetate pH 5.5. Fractions were collected and analyzed by SDS-PAGE using a NUPAGE® NOVEX® 4-12% Bis-Tris Gel with MES. Fractions containing a band at approximately 40 kDa were pooled and concentrated by ultrafiltration.

A 1600 ml volume of A. oryzae O5KRD supernatant was precipitated with ammonium sulfate (80% saturation), re-dissolved in 50 ml of 20 mM sodium acetate pH 5.5, dialyzed against the same buffer, and filtered through a 0.45 µm filter. The final volume was 60 ml. The solution was applied to a 40 ml Q SEPHAROSE® Fast Flow column equilibrated with 20 mM sodium acetate pH 5.0 and the proteins were eluted using a linear 0-0.5 M NaCl gradient. Fractions were collected and applied to a 40 ml Phenyl SEPHAROSE® 6 Fast Flow column (GE Healthcare Life Sciences, Piscataway, N.J., USA) and the proteins were eluted using a linear 1.2-0M $(NH_4)_2SO_4$ gradient. Fractions were collected and analyzed by SDS-PAGE using a NUPAGE® NOVEX® 4-12% Bis-Tris Gel with MES. Fractions containing a band at approximately 40 kDa were pooled and concentrated by ultrafiltration.

A 1600 ml volume of A. oryzae EXP02789 supernatant was precipitated with ammonium sulfate (80% saturation), re-dissolved in 50 ml of 25 mM Bis-Tris pH 6.0, dialyzed against the same buffer, and filtered through a 0.45 mm filter. The final volume was 60 ml. The solution was applied to a 40 ml Q SEPHAROSE® Fast Flow column equilibrated with 25 mM Bis-Tris pH 6.0 and the proteins were eluted with a linear 0-0.5 M NaCl gradient. Fractions were collected, pooled, dialyzed against 25 mM Bis-Tris pH5.5, applied to a 40 ml SP SEPHAROSE® Fast Flow column equilibrated with 25 mM Bis-Tris pH5.5, and the proteins were eluted with a linear 0-0.5 M NaCl gradient. Fractions were collected and analyzed by SDS-PAGE using a NUPAGE® NOVEX® 4-12% Bis-Tris Gel with MES. Fractions containing a band at approximately 34 kDa were pooled and concentrated by ultrafiltration.

A 2000 ml volume of A. oryzae 04S5C supernatant was precipitated with ammonium sulfate (80% saturation), re-dissolved in 50 ml of 20 mM Tris-HCl pH 7.5, dialyzed against the same buffer, and filtered through a 0.45 mm filter. The final volume was 80 ml. The solution was applied to a 40 ml Q SEPHAROSE® Fast Flow column equilibrated with 20 mM Tris-HCl pH7.5 and the proteins were eluted with a linear 0-0.5 M NaCl gradient. Fractions were collected and analyzed by SDS-PAGE using a NUPAGE® NOVEX® 4-12% Bis-Tris Gel with MES. Fractions containing a band at approximately 46 kDa were pooled and concentrated by ultrafiltration.

A 3200 ml volume of A. oryzae O7R3T supernatant was precipitated with ammonium sulfate (80% saturation) and re-dissolved in 50 ml 20 mM Bis-Tris pH6.5, dialyzed against the same buffer, and filtered through a 0.45 µm filter. The final volume was 110 ml. The solution was applied to a 40 ml Q SEPHAROSE® Fast Flow column equilibrated in 20 mM Bis-Tris pH 6.5, and the proteins was eluted with a linear 0.0-0.2M NaCl gradient. Fractions eluted with 0.1-0.2M NaCl were collected and further purified using a 40 ml Phenyl SEPHAROSE® 6 Fast Flow column with a linear 1.2-0 M $(NH_4)_2SO_4$ gradient. Fractions were evaluated by SDS-PAGE using a NUPAGE® NOVEX® 4-12% Bis-Tris Gel with MES. Fractions containing a band of approximately 42 kDa were pooled concentrated by ultrafiltration.

Example 16

Characterization of the Malbranchea cinnamomea P23DM4 GH10 Xylanase

Specific Activity.

The specific activity of the Malbranchea cinnamomea P23DM4 GH10 xylanase was determined using birchwood xylan (Sigma Chemical Co., St. Louis, Mo., USA) as substrate. A stock solution of the birchwood xylan was prepared by mixing 2 g of the birchwood xylan per liter of 50 mM sodium acetate pH 5.0 with 0.01% TWEEN® 20. To 190 µl of the birchwood xylan stock solution was added 10 µl of Malbranchea cinnamomea GH10 xylanase (at different protein loadings). Protein concentration was determined using a Microplate BCA™ Protein Assay Kit (Thermo Fischer Scientific, Waltham, Mass., USA) in which bovine serum albumin was used as a protein standard. A substrate control and enzyme control were included. The reaction was incubated at 50° C. for 30 minutes followed by addition of 50 µl of 0.5 M NaOH to stop the reaction. The reducing sugars produced were determined using a para-hydroxybenzoic acid hydrazide (PHBAH, Sigma Chemical Co., St. Louis, Mo., USA) assay adapted to a 96 well microplate format as described below. Briefly, a 100 µl aliquot of an appropriately diluted sample was placed in a 96-well conical bottomed microplate. Reactions were initiated by adding 50 µl of 1.5% (w/v) PHBAH in 2% NaOH to each well. Plates were heated uncovered at 95° C. for 10 minutes and then allowed to cool to room temperature (RT) before adding 50 µl of distilled water to each well. A 100 µl aliquot from each well was transferred to a flat bottomed 96 well plate and the absorbance at 410 nm was measured using a SPECTRAMAX® Microplate Reader (Molecular Devices, Sunnyvale, Calif., USA). Glucose standards (0.1-0.0125 mg/ml diluted with 0.4% sodium hydroxide) were used to prepare a standard curve to translate the obtained $A_{410nm}$ values into glucose equivalents. The enzyme loading versus the reducing sugars produced was plotted and the linear range was used to calculate the specific activity of the M. cinnamomea P23DM4 GH10 xylanase, as expressed as µmole of glucose equivalent produced per minute per mg enzyme, or IU/mg. The specific activity of the M. cinnamomea P23DM4 GH10 xylanase on birchwood xylan was measured as 53.2 IU/mg enzyme.

Thermostability.

The M. cinnamomea P23DM4 GH10 xylanase was diluted in 50 mM sodium acetate pH 5 containing 0.01% TWEEN® 20 to 1 g per liter, and then incubated at 50° C. for 3 days and 60° C. for 3 hours and 24 hours. The same sample was stored at 4° C. to serve as control. After incubation, the activity of the samples on birchwood xylan was measured, following the assay protocol above for determining specific activity except only one enzyme loading was used which gave <5% conversion in the specific activity assay. The activity of the sample at 4° C. was normalized to 100%, and the activities of samples under the other incubation conditions were compared to the 4° C. activity. The results of the thermostability determination are shown below.

| Incubation condition | Residual activity on birchwood xylan |
|---|---|
| 4° C. | 100% |
| 50° C., 3 days | 97% |
| 60° C., 3 hours | 6% |
| 60° C., 24 hours | 0% | pH Profile.

The pH activity profile of the *M. cinnamomea* P23DM4 GH10 xylanase was determined using the same protocol for determining the specific activity above, except the assay was performed at five different pHs (4, 5, 6, 7, and 8) and only one enzyme loading was used which gave <5% conversion in the specific activity assay. Britton Robinson buffer was used and prepared as follows: a 100 mM stock solution was made containing 0.1 mole of boric acid, 0.1 mole of acetic acid. and 0.1 mole of phosphoric acid in 1 liter of deionized water. The 100 mM stock solution was then titrated to 4, 5, 6, 7, or 8 using 5M NaOH and then diluted to 40 mM. The birchwood xylan was prepared in the same buffer, and the activity was measured at 50° C. The highest activity was normalized to 100%, and activities at the other pH values were compared to the highest activity and expressed in % activity. The results of the pH profile determination are shown below.

| pH value | % Activity |
|---|---|
| 4.0 | 1% |
| 5.0 | 81% |
| 6.0 | 100% |
| 7.0 | 78% |
| 8.0 | 37% |

Example 17

Measurement of Xylanase Activity

Xylanase activity was measured using AZCL-xylan (Megazyme, Bray, Ireland) as a substrate. A 0.2% AZCL-xylan suspension was prepared in 20 mM sodium acetate pH5.0 buffer with addition of 0.01% TRITON® X-100 by gentle stirring. Then 100 µl of the 0.2% AZCL-xylan suspension were mixed with 20 µl of the xylanase sample in a microtiter plate and placed on ice before reaction. The assay was initiated by transferring the microtiter plate to an Eppendorf® thermomixer, which was set to a temperature of 50° C. The plate was incubated for 15-30 minutes on the thermomixer at 700 rpm for a microtiter plate. The reaction was stopped by transferring the plate back to the ice bath. Then the plate was centrifuged at 1000 g in an ice cold centrifuge for a few minutes and 100 µl of supernatant were transferred to a microtiter plate. The absorbance at 595 nm was read as a measure of xylanase activity. All reactions were performed in triplicate and a buffer control without xylanase) was also performed.

The purified xylanases from *Aspergillus oryzae* expression strains O5KR9, O5KRD, O4S5C, and 07R3T (see Example 15) were assayed for xylanase activity as described above. The results are shown below.

| Protein | $OD_{595}$ |
|---|---|
| control | 0.1354 |
| O5KR9 | 1.539 |
| O5KRD | 0.9219 |
| O4S5C | 1.4541 |
| O7R3T | 1.2844 |

The present invention is further described by the following numbered paragraphs:

[1] An isolated polypeptide having xylanase activity, selected from the group consisting of: (a) a polypeptide having at least 60% sequence identity to the mature polypeptide of SEQ ID NO: 2; at least 65% sequence identity to the mature polypeptide of SEQ ID NO: 12; at least 70% sequence identity to the mature polypeptide of SEQ ID NO: 4 or SEQ ID NO: 10; at least 75% sequence identity to the mature polypeptide of SEQ ID NO: 14 or SEQ ID NO: 16; at least 80% sequence identity to the mature polypeptide of SEQ ID NO: 6 or SEQ ID NO: 8; at least 85% sequence identity to the mature polypeptide of SEQ ID NO: 20; or at least 90% sequence identity to the mature polypeptide of SEQ ID NO: 18; (b) a polypeptide encoded by a polynucleotide that hybridizes under at least medium-high stringency conditions with (i) the mature polypeptide coding sequence of SEQ ID NO: 1, SEQ ID NO: 3, SEQ ID NO: 9, or SEQ ID NO: 11, (ii) the cDNA sequence of SEQ ID NO: 1, SEQ ID NO: 3, SEQ ID NO: 9, or SEQ ID NO: 11, or (iii) the full-length complement of (i) or (ii); or at least high stringency conditions with (i) the mature polypeptide coding sequence of SEQ ID NO: 5, SEQ ID NO: 7, SEQ ID NO: 13, SEQ ID NO: 15, SEQ ID NO: 17, or SEQ ID NO: 19, (ii) the cDNA sequence of SEQ ID NO: 5, SEQ ID NO: 13, SEQ ID NO: 17, or SEQ ID NO: 19, or (iii) the full-length complement of (i) or (ii); (c) a polypeptide encoded by a polynucleotide having at least 60% sequence identity to the mature polypeptide coding sequence of SEQ ID NO: 1 or the cDNA sequence thereof; at least 65% sequence identity to the mature polypeptide coding sequence of SEQ ID NO: 11 or the cDNA sequence thereof; at least 70% sequence identity to the mature polypeptide coding sequence of SEQ ID NO: 3 or the cDNA sequence thereof or the mature polypeptide coding sequence of SEQ ID NO: 9 or the cDNA sequence thereof; at least 75% sequence identity to the mature polypeptide coding sequence of SEQ ID NO: 13 or the cDNA sequence thereof or the mature polypeptide coding sequence of SEQ ID NO: 15; at least 80% sequence identity to the mature polypeptide coding sequence of SEQ ID NO: 5 or the cDNA sequence thereof or the mature polypeptide coding sequence of SEQ ID NO: 7; at least 85% sequence identity to the mature polypeptide coding sequence of SEQ ID NO: 19 or the cDNA sequence thereof; or at least 90% sequence identity to the mature polypeptide coding sequence of SEQ ID NO: 17 or the cDNA sequence thereof; (d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 comprising a substitution, deletion, and/or insertion at one or more (e.g., several) positions; and (e) a fragment of the polypeptide of (a), (b), (c), or (d) that has xylanase activity.

[2] The polypeptide of paragraph 1, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 12; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4 or SEQ ID NO: 10; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14 or SEQ ID NO: 16; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6 or SEQ ID NO: 8; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20; or at least 90%, at least 91%, at least 92%, at least 93%, at least 94%, at least 95%, at least 96%, at least 97%, at least 98%, at least 99%, or 100% sequence identity to the mature polypeptide of SEQ ID NO: 18.

[3] The polypeptide of paragraph 1 or 2, which is encoded by a polynucleotide that hybridizes under medium-high, high, or very high stringency conditions with (i) the mature polypeptide coding sequence of SEQ ID NO: 1, SEQ ID NO: 3, SEQ ID NO: 9, or SEQ ID NO: 11, (ii) the cDNA sequence of SEQ ID NO: 1, SEQ ID NO: 3, SEQ ID NO: 9, or SEQ ID NO: 11, or (iii) the full-length complement of (i) or (ii); or high or very high stringency conditions with (i) the mature polypeptide coding sequence of SEQ ID NO: 5, SEQ ID NO: 7, SEQ ID NO: 13, SEQ ID NO: 15, SEQ ID NO: 17, or SEQ ID NO: 19, (ii) the cDNA sequence of SEQ ID NO: 5, SEQ ID NO: 13, SEQ ID NO: 17, or SEQ ID NO: 19, or (iii) the full-length complement of (i) or (ii).

[4] The polypeptide of any of paragraphs 1-3, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 11 or the cDNA sequence thereof; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof or the mature polypeptide coding sequence of SEQ ID NO: 9 or the cDNA sequence thereof; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13 or the cDNA sequence thereof or the mature polypeptide coding sequence of SEQ ID NO: 15; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof or the mature polypeptide coding sequence of SEQ ID NO: 7; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 19 or the cDNA sequence thereof; or at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17 or the cDNA sequence thereof.

[5] The polypeptide of any of paragraphs 1-4, comprising or consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 or the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20.

[6] The polypeptide of paragraph 5, wherein the mature polypeptide is amino acids 21 to 406 of SEQ ID NO: 2, amino acids 18 to 360 of SEQ ID NO: 4, amino acids 19 to 376 of SEQ ID NO: 6, amino acids 23 to 367 of SEQ ID NO: 8, amino acids 19 to 326 of SEQ ID NO: 10, amino acids 21 to 354 of SEQ ID NO: 12, amino acids 18 to 355 of SEQ ID NO: 14, amino acids 20 to 366 of SEQ ID NO: 16, amino acids 18 to 381 of SEQ ID NO: 18, or amino acids 18 to 362 of SEQ ID NO: 20.

[7] The polypeptide of any of paragraphs 1-4, which is a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20 comprising a substitution, deletion, and/or insertion at one or more positions.

[8] The polypeptide of any of paragraphs 1-7, which is a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20, wherein the fragment has xylanase activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: cultivating a cell, which in its wild-type form produces the polypeptide, under conditions conducive for production of the polypeptide.

[14] The method of paragraph 13, further comprising recovering the polypeptide.

[15] A method of producing a polypeptide having xylanase activity, comprising: cultivating the host cell of paragraph 12 under conditions conducive for production of the polypeptide.

[16] The method of paragraph 15, further comprising recovering the polypeptide.

[17] A transgenic plant, plant part or plant cell transformed with a polynucleotide encoding the polypeptide of any of paragraphs 1-8.

[18] A method of producing a polypeptide having xylanase activity, comprising: cultivating the transgenic plant or plant cell of paragraph 17 under conditions conducive for production of the polypeptide.

[19] The method of paragraph 18, further comprising recovering the polypeptide.

[20] A method of producing a mutant of a parent cell, comprising inactivating a polynucleotide encoding the polypeptide of any of paragraphs 1-8, which results in the mutant producing less of the polypeptide than the parent cell.

[21] A mutant cell produced by the method of paragraph 20.

[22] The mutant cell of paragraph 21, further comprising a gene encoding a native or heterologous protein.

[23] A method of producing a protein, comprising: cultivating the mutant cell of paragraph 21 or 22 under conditions conducive for production of the protein.

[24] The method of paragraph 23, further comprising recovering the polypeptide.

[25] A double-stranded inhibitory RNA (dsRNA) molecule comprising a subsequence of the polynucleotide of paragraph 10, wherein optionally the dsRNA is an siRNA or an miRNA molecule.

[26] The double-stranded inhibitory RNA (dsRNA) molecule of paragraph 25, which is about 15, 16, 17, 18, 19, 20, 21, 22, 23, 24, 25 or more duplex nucleotides in length.

[27] A method of inhibiting the expression of a polypeptide having xylanase activity in a cell, comprising administering to the cell or expressing in the cell the double-stranded inhibitory RNA (dsRNA) molecule of paragraph 25 or 26.

[28] A cell produced by the method of paragraph 27.

[29] The cell of paragraph 28, further comprising a gene encoding a native or heterologous protein.

[30] A method of producing a protein, comprising: cultivating the cell of paragraph 28 or 29 under conditions conducive for production of the protein.

[31] The method of paragraph 30, further comprising recovering the polypeptide.

[32] An isolated polynucleotide encoding a signal peptide comprising or consisting of amino acids 1 to 20 of SEQ ID NO: 2, amino acids 1 to 17 of SEQ ID NO: 4, amino acids 1 to 18 of SEQ ID NO: 6, amino acids 1 to 22 of SEQ ID NO: 8, amino acids 1 to 18 of SEQ ID NO: 10, amino acids 1 to 20 of SEQ ID NO: 12, amino acids 1 to 17 of SEQ ID NO: 14, amino acids 1 to 19 of SEQ ID NO: 16, amino acids 1 to 17 of SEQ ID NO: 18, or amino acids 1 to 17 of SEQ ID NO: 20.

[33] A nucleic acid construct or expression vector comprising a gene encoding a protein operably linked to the polynucleotide of paragraph 32, wherein the gene is foreign to the polynucleotide encoding the signal peptide.

[34] A recombinant host cell comprising a gene encoding a protein operably linked to the polynucleotide of paragraph 32, wherein the gene is foreign to the polynucleotide encoding the signal peptide.

[35] A method of producing a protein, comprising: cultivating a recombinant host cell comprising a gene encoding a protein operably linked to the polynucleotide of paragraph 32, wherein the gene is foreign to the polynucleotide encoding the signal peptide, under conditions conducive for production of the protein.

[36] The method of paragraph 35, further comprising recovering the polypeptide.

[37] A process for degrading a cellulosic or xylan-containing material, comprising: treating the cellulosic or xylan-containing material with an enzyme composition in the presence of the polypeptide having xylanase activity of any of paragraphs 1-8.

[38] The process of paragraph 37, wherein the cellulosic or xylan-containing material is pretreated.

[39] The process of paragraph 37 or 38, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[40] The process of paragraph 39, wherein the cellulase is one or more enzymes selected from the group consisting of an endoglucanase, a cellobiohydrolase, and a beta-glucosidase.

[41] The process of paragraph 39, wherein the hemicellulase is one or more enzymes selected from the group consisting of a xylanase, an acetylxylan esterase, a feruloyl esterase, an arabinofuranosidase, a xylosidase, and a glucuronidase.

[42] The process of any of paragraphs 37-41, further comprising recovering the degraded cellulosic or xylan-containing material.

[43] The process of paragraph 42, wherein the degraded cellulosic or xylan-containing material is a sugar.

[44] The process of paragraph 43, wherein the sugar is selected from the group consisting of glucose, xylose, mannose, galactose, and arabinose.

[45] A process for producing a fermentation product, comprising: (a) saccharifying a cellulosic or xylan-containing material with an enzyme composition in the presence of the polypeptide having xylanase activity of any of paragraphs 1-8; (b) fermenting the saccharified cellulosic or xylan-containing material with one or more fermenting microorganisms to produce the fermentation product; and (c) recovering the fermentation product from the fermentation.

[46] The process of paragraph 45, wherein the cellulosic or xylan-containing material is pretreated.

[47] The process of paragraph 45 or 46, wherein the enzyme composition comprises the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[48] The process of paragraph 47, wherein the cellulase is one or more enzymes selected from the group consisting of an endoglucanase, a cellobiohydrolase, and a beta-glucosidase.

[49] The process of paragraph 47, wherein the hemicellulase is one or more enzymes selected from the group consisting of a xylanase, an acetylxylan esterase, a feruloyl esterase, an arabinofuranosidase, a xylosidase, and a glucuronidase.

[50] The process of any of paragraphs 45-49, wherein steps (a) and (b) are performed simultaneously in a simultaneous saccharification and fermentation.

[51] The process of any of paragraphs 45-50, wherein the fermentation product is an alcohol, an alkane, a cycloalkane, an alkene, an amino acid, a gas, isoprene, a ketone, an organic acid, or polyketide.

[52] A process of fermenting a cellulosic or xylan-containing material, comprising: fermenting the cellulosic or xylan-containing material with one or more fermenting microorganisms, wherein the cellulosic or xylan-containing material is saccharified with an enzyme composition in the presence of the polypeptide having xylanase activity of any of paragraphs 1-8.

[53] The process of paragraph 52, wherein the fermenting of the cellulosic or xylan-containing material produces a fermentation product.

[54] The process of paragraph 53, further comprising recovering the fermentation product from the fermentation.

[55] The process of paragraph 53 or 54, wherein the fermentation product is an alcohol, an alkane, a cycloalkane, an alkene, an amino acid, a gas, isoprene, a ketone, an organic acid, or polyketide.

[56] The process of any of paragraphs 52-55, wherein the cellulosic or xylan-containing material is pretreated before saccharification.

[57] The process of any of paragraphs 52-56, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[58] The process of paragraph 57, wherein the cellulase is one or more enzymes selected from the group consisting of an endoglucanase, a cellobiohydrolase, and a beta-glucosidase.

[59] The process of paragraph 57, wherein the hemicellulase is one or more enzymes selected from the group consisting of a xylanase, an acetylxylan esterase, a feruloyl esterase, an arabinofuranosidase, a xylosidase, and a glucuronidase.

[60] A whole broth formulation or cell culture composition comprising the polypeptide of any of paragraphs 1-8.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a polypeptide having xylanase activity, wherein the polynucleotide is operably linked to one or more heterologous control sequences that direct the production of the polypeptide having xylanase activity in a recombinant host cell, and wherein the polypeptide having xylanase activity is selected from the group consisting of:
   (a) a polypeptide having at least 90% sequence identity to the mature polypeptide of SEQ ID NO: 10:
   (b) a polypeptide encoded by a polynucleotide that hybridizes under high stringency conditions with the full-length complement of the mature polypeptide coding sequence of SEQ ID NO: 9, wherein the high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; and
   (c) a polypeptide encoded by a polynucleotide having at least 90% sequence identity to the mature polypeptide coding sequence of SEQ ID NO: 9.

2. A recombinant host cell transformed with the nucleic acid construct of claim 1.

3. A method of producing a polypeptide having xylanase activity, comprising:
   (a) cultivating the recombinant host cell of claim 2 under conditions conducive for production of the polypeptide; and optionally
   (b) recovering the polypeptide.

4. The nucleic acid construct of claim 1, wherein the polypeptide having xylanase comprises an amino acid sequence having at least 95% sequence identity to the mature polypeptide of SEQ ID NO: 10.

5. The nucleic acid construct of claim 1, wherein the polypeptide having xylanase comprises an amino acid sequence having at least 96% sequence identity to the mature polypeptide of SEQ ID NO: 10.

6. The nucleic acid construct of claim 1, wherein the polypeptide having xylanase comprises an amino acid sequence having at least 97% sequence identity to the mature polypeptide of SEQ ID NO: 10.

7. The nucleic acid construct of claim 1, wherein the polypeptide having xylanase comprises an amino acid sequence having at least 98% sequence identity to the mature polypeptide of SEQ ID NO: 10.

8. The nucleic acid construct of claim 1, wherein the polypeptide having xylanase comprises an amino acid sequence having at least 99% sequence identity to the mature polypeptide of SEQ ID NO: 10.

9. The nucleic acid construct of claim 1, wherein the polypeptide having xylanase activity comprises SEQ ID NO: 10 or the mature polypeptide of SEQ ID NO: 10.

10. The nucleic acid construct of claim 1, wherein the polypeptide having xylanase is encoded by a polynucleotide that hybridizes under very high stringency conditions with the full-length complement of nucleotides 58 to 912 of the polynucleotide of SEQ ID NO: 9, wherein the very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

11. An isolated recombinant host cell transformed with a nucleic acid construct comprising a polynucleotide encoding a polypeptide having xylanase activity, wherein the polynucleotide is operably linked to one or more control sequences that direct the production of the polypeptide, wherein the polypeptide having xylanase activity is heterologous to the recombinant host cell, and wherein the polypeptide having xylanase activity is selected from the group consisting of:
   (a) a polypeptide having at least 90% sequence identity to the mature polypeptide of SEQ ID NO: 10;
   (b) a polypeptide encoded by a polynucleotide that hybridizes under high stringency conditions with the full-length complement of the mature polypeptide coding sequence of SEQ ID NO: 9, wherein the high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; and
   (c) a polypeptide encoded by a polynucleotide having at least 90% sequence identity to the mature polypeptide coding sequence of SEQ ID NO: 9.

12. The recombinant host cell of claim 11, wherein the polypeptide having xylanase comprises an amino acid sequence having at least 95% sequence identity to the mature polypeptide of SEQ ID NO: 10.

13. The recombinant host cell of claim 11, wherein the polypeptide having xylanase comprises an amino acid sequence having at least 96% sequence identity to the mature polypeptide of SEQ ID NO: 10.

14. The recombinant host cell of claim 11, wherein the polypeptide having xylanase comprises an amino acid sequence having at least 97% sequence identity to the mature polypeptide of SEQ ID NO: 10.

15. The recombinant host cell of claim 11, wherein the polypeptide having xylanase comprises an amino acid sequence having at least 98% sequence identity to the mature polypeptide of SEQ ID NO: 10.

16. The recombinant host cell of claim 11, wherein the polypeptide having xylanase comprises an amino acid sequence having at least 99% sequence identity to the mature polypeptide of SEQ ID NO: 10.

17. The recombinant host cell of claim 11, wherein the polypeptide having xylanase comprises SEQ ID NO: 10 or the mature polypeptide of SEQ ID NO: 10.

18. The recombinant host cell of claim 11, wherein the polypeptide having xylanase is encoded by a polynucleotide that hybridizes under very high stringency conditions with the full-length complement of nucleotides 58 to 912 of the polynucleotide of SEQ ID NO: 9, wherein the very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

19. A method for producing a polypeptide having xylanase having cellulolytic enhancing activity, comprising (a) cultivating the recombinant host cell of claim 11 under conditions conducive for production of the polypeptide; and optionally (b) recovering the polypeptide.

* * * * *

SEQUENCE LISTING

```
<160> NUMBER OF SEQ ID NOS: 41

<210> SEQ ID NO 1
<211> LENGTH: 1314
<212> TYPE: DNA
<213> ORGANISM: Scytalidium thermophilum

<400> SEQUENCE: 1
atggcgaggc tctctcgcgc cctgctggcg gctgccgccg tagccgccaa tgtctcggcg      60
caacagcaac aacaagcaca agaacagctc cccgagggat tgcacggcct catggtggcc     120
gccggcaagg agtatttcgg cacggcgacc gatgtcaaca gcatcgacga cgagatatat     180
cagtccatcc tcaactacca gggcgagttc ggcatggtga cgcccgaaaa ctcgcaaaag     240
tgggagttta ctcaacctcg tcgggacgag ttcgtctaca ccaacgccga caccgtcgtt     300
gggagggcac aagagattgg gcaattagta cgatgccacg ccttgacatg gcattctcaa     360
ttgccgacgt ttggtatgta ttcccctccg ccatttcaaa gccatcatcg gcgatgtgtt     420
ccacgccttt actgacatgg agtttttctt ctcccctcc ttccagtctc aaccacgcaa     480
tggaatgctt ccactctcgc ctctttccta accaccaca tcgacaacgt cgtgacccac     540
ttcgccgggc aatgctacgc ctgggacgtg gtcaacgagg cgttaaacga agacgggtcc     600
tatcgaaact ctacctttta ccaatacctg ggcgaggagt acatcacgat ctccttcgag     660
gcggccgcca aagccgaccc ggccgccaag ctctactata acgacttcaa cctcgaaacc     720
tcaccgaaaa aggctgccgg tgccgagcgc atcgtccgtc tcctccagga cgccggcgcg     780
cgcatcgacg gcgtcggctt ccaggccac ctcgtcgtgg gccaaacccc gccgcgcaag     840
```

```
aacctcaccg ccctcctgtc gcgcttcgcc agcctcggcg ttgaggtggc ctacacggag    900
ctcgacattg ctcacgagtt ccccaaagac agctccaacc ggaccccgga cgccgcggcg    960
ctcgagcagc aagccgaaga ctacgtcgcc gtcgttgggt cgtgcctgga cgagcccaaa   1020
tgcgtcggcg tcacggtctg gcagttcacc gacgagtaca gctgggtccc ggaaacgttt   1080
gaaggccgcg accaggcgtg cttgtggacg cgcgactaca agaagaagcc ggcctacgac   1140
gccgtgtcca atctgctgcg cgaagcggca gccaacaaca cgggcgtgaa caccaactcg   1200
actgaggata tcccggagcc gataccctcc aacggggcag cggcggcagc gggcggttgg   1260
gtggccaggg ttgctctggg agcggccttg gttgtgggga tggctttgct ttaa         1314
```

<210> SEQ ID NO 2
<211> LENGTH: 406
<212> TYPE: PRT
<213> ORGANISM: Scytalidium thermophilum

<400> SEQUENCE: 2

```
Met Ala Arg Leu Ser Arg Ala Leu Leu Ala Ala Ala Val Ala Ala
1               5                   10                  15

Asn Val Ser Ala Gln Gln Gln Gln Ala Gln Glu Gln Leu Pro Glu
                20                  25                  30

Gly Leu His Gly Leu Met Val Ala Ala Gly Lys Glu Tyr Phe Gly Thr
            35                  40                  45

Ala Thr Asp Val Asn Ser Ile Asp Asp Glu Ile Tyr Gln Ser Ile Leu
        50                  55                  60

Asn Tyr Gln Gly Glu Phe Gly Met Val Thr Pro Glu Asn Ser Gln Lys
65                  70                  75                  80

Trp Glu Phe Thr Gln Pro Arg Arg Asp Glu Phe Val Tyr Thr Asn Ala
                85                  90                  95

Asp Thr Val Val Gly Arg Ala Gln Glu Ile Gly Gln Leu Val Arg Cys
            100                 105                 110

His Ala Leu Thr Trp His Ser Gln Leu Pro Thr Phe Val Ser Thr Thr
        115                 120                 125

Gln Trp Asn Ala Ser Thr Leu Ala Ser Phe Leu Thr Thr His Ile Asp
    130                 135                 140

Asn Val Val Thr His Phe Ala Gly Gln Cys Tyr Ala Trp Asp Val Val
145                 150                 155                 160

Asn Glu Ala Leu Asn Glu Asp Gly Ser Tyr Arg Asn Ser Thr Phe Tyr
                165                 170                 175

Gln Tyr Leu Gly Glu Glu Tyr Ile Thr Ile Ser Phe Glu Ala Ala
            180                 185                 190

Lys Ala Asp Pro Ala Ala Lys Leu Tyr Tyr Asn Asp Phe Asn Leu Glu
        195                 200                 205

Thr Ser Pro Lys Lys Ala Ala Gly Ala Glu Arg Ile Val Arg Leu Leu
    210                 215                 220

Gln Asp Ala Gly Ala Arg Ile Asp Gly Val Gly Phe Gln Ala His Leu
225                 230                 235                 240

Val Val Gly Gln Thr Pro Pro Arg Lys Asn Leu Thr Ala Leu Leu Ser
                245                 250                 255

Arg Phe Ala Ser Leu Gly Val Glu Val Ala Tyr Thr Glu Leu Asp Ile
            260                 265                 270

Ala His Glu Phe Pro Lys Asp Ser Ser Asn Arg Thr Pro Asp Ala Ala
        275                 280                 285

Ala Leu Glu Gln Gln Ala Glu Asp Tyr Val Ala Val Val Gly Ser Cys
```

```
                         290                 295                 300

Leu Asp Glu Pro Lys Cys Val Gly Val Thr Val Trp Gln Phe Thr Asp
305                 310                 315                 320

Glu Tyr Ser Trp Val Pro Glu Thr Phe Glu Gly Arg Asp Gln Ala Cys
                325                 330                 335

Leu Trp Thr Arg Asp Tyr Lys Lys Pro Ala Tyr Asp Ala Val Ser
            340                 345                 350

Asn Leu Leu Arg Glu Ala Ala Asn Asn Thr Gly Val Asn Thr Asn
        355                 360                 365

Ser Thr Glu Asp Ile Pro Glu Pro Ile Pro Ser Asn Gly Ala Ala
    370                 375                 380

Ala Ala Gly Gly Trp Val Ala Arg Val Ala Leu Gly Ala Ala Leu Val
385                 390                 395                 400

Val Gly Met Ala Leu Leu
                405

<210> SEQ ID NO 3
<211> LENGTH: 1350
<212> TYPE: DNA
<213> ORGANISM: Scytalidium thermophilum

<400> SEQUENCE: 3
atgcgtttct ccgcctccct gctccttgcc ctgacgggct ccgctgccgc cagccctatc      60
cgggctgagg aagagatccg ggtgtacgac ttgcccatct cactgttcga tgatcgtcag     120
gctgacaaat gatgcagggc cttcacgccc gccaagtgc agggtctgga tgctgccatg      180
aaggctgccg aagggagta catcggcacc tccctcaccg tgaggaacga cttccaggag      240
cagaacatca tccgcactga gttcggctcg atcacgcccg agaacgccca gaagtgggac     300
gccaccgagc ccaaccgcgg ccagtttacc ttcggctctg ccgaccagca catggactgg     360
gcccgccaga cgggaagca cgtccgctgc acacccttg tctggtactc ccagctcccc      420
ggctgggtgt ccaacagcgg cttcaacaac gccaccttgc agcaggtgat gcagaatcac     480
atcaaccaag tgatgggccg gtaccgtggc cgctgcaacc actgggatgt cgtcaatgag     540
ggtatgtggt caaacattcc atgcatcgca gtcctttatc tccctgatat cagagtgaca     600
tttgctgaca ttttggcaaa gcgctgaacg aggatggcac ctaccgtgac aatgttttcc     660
tccgagtggt aggagagaaa ccctaaccct atccccaacc tgttgttttt caagctccca     720
ggctgatggc catgcgattg cagatcggag aggcgtatat cccgattgct ttcaggatgg     780
ccgcccaggc cgatccctcg gccaagctct actacaatga ctacaacctc gagtatctcg     840
gacccaaggt tgagggtgct gcccgcatcg tgcgccttgt caagcagtac ggcgctcgca     900
tcgacggtgt cggctatcag gctccacctt gtcaccgagcc caccccgact cagtccaccc     960
cgactccgtc tgaggaggac ctcatcaagg ctctgcgtat caccgctgac tcggtgtcg    1020 atgtcgccta caccgagatt gatatccgca tgccacccc gtcgaacgcc agaagctcc    1080 agcagcttgc ggatgcttac taccgcgtgg ctcgctcgtg catgaaggtt ccgcgctgcg    1140
tcggcatgac catttgggta agtccagacc tccatgaca gaggcactcc gatcaagcgc    1200
taactccgtg tgtagggcgt cactgaccgg tactcgtggg ttcccaacac cttccgcggt    1260
gagggtgatg cgctcctttg ggacagcaac taccagagga aggccgctta caacgctttc    1320
ctccgcggca tccaggagcc cgtcaactaa                                     1350

<210> SEQ ID NO 4
```

```
<211> LENGTH: 360
<212> TYPE: PRT
<213> ORGANISM: Scytalidium thermophilum

<400> SEQUENCE: 4

Met Arg Phe Ser Ala Ser Leu Leu Ala Leu Thr Gly Ser Ala Ala
1               5                   10                  15

Ala Ser Pro Ile Arg Ala Glu Glu Ile Arg Val Ala Phe Thr Pro
                20                  25                  30

Arg Gln Val Gln Gly Leu Asp Ala Met Lys Ala Ala Gly Arg Glu
            35                  40                  45

Tyr Ile Gly Thr Ser Leu Thr Val Arg Asn Asp Phe Gln Glu Gln Asn
50                      55                  60

Ile Ile Arg Thr Glu Phe Gly Ser Ile Thr Pro Glu Asn Ala Gln Lys
65                  70                  75                  80

Trp Asp Ala Thr Glu Pro Asn Arg Gly Gln Phe Thr Phe Gly Ser Ala
                85                  90                  95

Asp Gln His Met Asp Trp Ala Arg Gln Asn Gly Lys His Val Arg Cys
                100                 105                 110

His Thr Leu Val Trp Tyr Ser Gln Leu Pro Gly Trp Val Ser Asn Ser
            115                 120                 125

Gly Phe Asn Asn Ala Thr Leu Gln Gln Val Met Gln Asn His Ile Asn
130                 135                 140

Gln Val Met Gly Arg Tyr Arg Gly Arg Cys Asn His Trp Asp Val Val
145                 150                 155                 160

Asn Glu Ala Leu Asn Glu Asp Gly Thr Tyr Arg Asp Asn Val Phe Leu
                165                 170                 175

Arg Val Ile Gly Glu Ala Tyr Ile Pro Ile Ala Phe Arg Met Ala Ala
            180                 185                 190

Gln Ala Asp Pro Ser Ala Lys Leu Tyr Tyr Asn Asp Tyr Asn Leu Glu
        195                 200                 205

Tyr Leu Gly Pro Lys Val Glu Gly Ala Ala Arg Ile Val Arg Leu Val
210                 215                 220

Lys Gln Tyr Gly Ala Arg Ile Asp Gly Val Gly Tyr Gln Ala His Leu
225                 230                 235                 240

Val Thr Glu Pro Thr Pro Thr Gln Ser Thr Pro Thr Pro Ser Glu Glu
                245                 250                 255

Asp Leu Ile Lys Ala Leu Arg Ile Thr Ala Asp Leu Gly Val Asp Val
            260                 265                 270

Ala Tyr Thr Glu Ile Asp Ile Arg Met Arg Thr Pro Ser Asn Ala Gln
        275                 280                 285

Lys Leu Gln Gln Leu Ala Asp Ala Tyr Tyr Arg Val Ala Arg Ser Cys
290                 295                 300

Met Lys Val Pro Arg Cys Val Gly Met Thr Ile Trp Gly Val Thr Asp
305                 310                 315                 320

Arg Tyr Ser Trp Val Pro Asn Thr Phe Arg Gly Glu Gly Asp Ala Leu
                325                 330                 335

Leu Trp Asp Ser Asn Tyr Gln Arg Lys Ala Ala Tyr Asn Ala Phe Leu
            340                 345                 350

Arg Gly Ile Gln Glu Pro Val Asn
        355                 360

<210> SEQ ID NO 5
<211> LENGTH: 1199
<212> TYPE: DNA
```

<213> ORGANISM: Scytalidium thermophilum

<400> SEQUENCE: 5

```
atgcatctcg cttcgtcgct ctttctgctc gccactctgc ccttcggctt cgctgctggc    60
aagggcaagg gcaagggcaa ggacaacagc gatgttggcc tcgacgtcct ggccaaaaag   120
gctggtctga agtacttcgg tgccgccacc gacacgcccg ccagcgggga gcgcgccggt   180
cttgaggata aatatcccga gtatgacagg atcatgtggc attcgcccga gttcggctcg   240
accacgccca ccaacggcca gaaggtcagt tgcaggccca gtcccggtgc accacttcta   300
tggatagtat caatactgac atgctccttc agtggctgtt tgttgagccc gagcgcggcg   360
tcttcaactt cacagagggc gacgtcgttg cctccaaggc ccgccagcac ggcaagctgc   420
tgcgctgcca cgctctcgtc tggcacagcc agctggctcc ctgggtcgag gagaccgagt   480
ggactccgga ggagctgcgc aaggtcatcg tcgaccacat caccgccgtc gccggccact   540
acaagggcca gtgctacgcc tgggacgttg tcaacgaggc gctgaacgag acggaacct    600
accgcgagag cgttttctac aaggttctcg gcgaggagta catcaagctt gccttcgaga   660
ccgccgccaa ggtcgaccct aaggccaagc tctactacaa cgactacaac ctcgagtggc   720
cctcggccaa gacggagggc gccaagcgca tcgtcaagct cctcaaggac gccaagatcc   780
ccatccacgg cgtcggcctg caggcccacc tcatcgccga gcagcacccc acgctcgacg   840
accacattgc cgccatccgc ggcttcaccc agctcggcgt cgaggtggct ctcaccgagc   900
tcgacatccg cctcaagacc ccggccaccg aggagaacct tgccctgcag cgcgaggcct   960
acaagaacgt cgtcggcgcc tgcgtccagg tctgcggctg cgtcggtgtc accatctggg  1020
acttctatga tcccttcagc tgggtcccct acttcttcga gggcgagggt gctcccctcc  1080
tgtggttcga ggacttcagc aagcaccccg cctactacgg cgtcgttgag gccctcacca  1140
acaagactcg ccgctcgaag cgcagcattt cggaccgccg ggccaagctc ctggcttaa   1199
```

<210> SEQ ID NO 6
<211> LENGTH: 376
<212> TYPE: PRT
<213> ORGANISM: Scytalidium thermophilum

<400> SEQUENCE: 6

```
Met His Leu Ala Ser Ser Leu Phe Leu Ala Thr Leu Pro Phe Gly
1               5                   10                  15

Phe Ala Ala Gly Lys Gly Lys Gly Lys Asp Asn Ser Asp Val
            20                  25                  30

Gly Leu Asp Val Leu Ala Lys Lys Ala Gly Leu Lys Tyr Phe Gly Ala
        35                  40                  45

Ala Thr Asp Thr Pro Gly Gln Arg Glu Arg Ala Gly Leu Glu Asp Lys
    50                  55                  60

Tyr Pro Glu Tyr Asp Arg Ile Met Trp His Ser Pro Glu Phe Gly Ser
65                  70                  75                  80

Thr Thr Pro Thr Asn Gly Gln Lys Trp Leu Phe Val Glu Pro Glu Arg
                85                  90                  95

Gly Val Phe Asn Phe Thr Glu Gly Asp Val Val Ala Ser Lys Ala Arg
            100                 105                 110

Gln His Gly Lys Leu Leu Arg Cys His Ala Leu Val Trp His Ser Gln
        115                 120                 125

Leu Ala Pro Trp Val Glu Glu Thr Glu Trp Thr Pro Glu Glu Leu Arg
    130                 135                 140
```

Lys Val Ile Val Asp His Ile Thr Ala Val Ala Gly His Tyr Lys Gly
145                 150                 155                 160

Gln Cys Tyr Ala Trp Asp Val Val Asn Glu Ala Leu Asn Glu Asp Gly
            165                 170                 175

Thr Tyr Arg Glu Ser Val Phe Tyr Lys Val Leu Gly Glu Tyr Ile
        180                 185                 190

Lys Leu Ala Phe Glu Thr Ala Ala Lys Val Asp Pro Lys Ala Lys Leu
    195                 200                 205

Tyr Tyr Asn Asp Tyr Asn Leu Glu Trp Pro Ser Ala Lys Thr Glu Gly
210                 215                 220

Ala Lys Arg Ile Val Lys Leu Leu Lys Asp Ala Lys Ile Pro Ile His
225                 230                 235                 240

Gly Val Gly Leu Gln Ala His Leu Ile Ala Glu Gln His Pro Thr Leu
            245                 250                 255

Asp Asp His Ile Ala Ala Ile Arg Gly Phe Thr Gln Leu Gly Val Glu
            260                 265                 270

Val Ala Leu Thr Glu Leu Asp Ile Arg Leu Lys Thr Pro Ala Thr Glu
            275                 280                 285

Glu Asn Leu Ala Leu Gln Arg Glu Ala Tyr Lys Asn Val Val Gly Ala
290                 295                 300

Cys Val Gln Val Cys Gly Cys Val Gly Val Thr Ile Trp Asp Phe Tyr
305                 310                 315                 320

Asp Pro Phe Ser Trp Val Pro Tyr Phe Phe Glu Gly Glu Gly Ala Pro
            325                 330                 335

Leu Leu Trp Phe Glu Asp Phe Ser Lys His Pro Ala Tyr Tyr Gly Val
            340                 345                 350

Val Glu Ala Leu Thr Asn Lys Thr Arg Arg Ser Lys Arg Ser Ile Ser
            355                 360                 365

Asp Arg Arg Ala Lys Leu Leu Ala
370                 375

<210> SEQ ID NO 7
<211> LENGTH: 1104
<212> TYPE: DNA
<213> ORGANISM: Scytalidium thermophilum

<400> SEQUENCE: 7

| | |
|---|---:|
| atgagagctc cgtcctccgt cgctgccgcg actgccctcc tcttgctggc cacccccgcg | 60 |
| acggcgcagc ttcacaaact cgctgtccag gcgggtctcc gctacttcgg cgcggccacc | 120 |
| gacactcctc accagcgtga gcgcgccccc tacccggagt cctatccgca gtacgacgcc | 180 |
| atcctggcca caacgacga attcgggcaa accacgccga ccaacgggca gaagtggctc | 240 |
| ttcaccgaac ctgccccgcg cctcttcaac ttcaccgagg cgactacgt cgccgacctg | 300 |
| gcagcgtcgc agggcaagct ccttcggtgc acgccctcg tctggcacag ccagctcgct | 360 |
| ccctgggttg aggagaccaa ctggaccgcg cccgccctgg ctgacgccat gagcgtcac | 420 |
| atccgcgccg tcgcgggcta ctaccgtgga agatgccatg cgtgggatgt tgtcaatgag | 480 |
| gcgctagacg aggacgggtc ctatcgccag tccattttct accgggtgct ggggaggag | 540 |
| tatcttcgcc tggctttccg ggccgcgcg ccgcggacc ctgacgcgaa gctgtactac | 600 |
| aacgactacg gcatcgagcg accaacttcc cccaagacgg ctggtgccct gaggcttgtg | 660 |
| aagatgttga aggatgccgg gctgcgagtg atggcgtcg gtatgcaggc gcatctccat | 720 |
| gccgacaatc acccgagtgc cgaggacctc attgccacaa gtgaggcata tgcggaactt | 780 |

```
gtcgacgagg ttgccttcac ggagctcgac gtgcgcatta acttcccgt ggacgagcag    840 aaactgcagt ggcagaagga atgctaccaa aagtggtga cggcgtgcgt gaaggtgaag     900
gcttgcgtgg gaattactct ctgggacttt tacgatccct tcagctgggt cccgcatgtg    960
ttcccgaaca atggagcgtc cctgttgtgg ttcgaggact ctcgaaaca cccggcttat    1020 gacggtatta ttgagacctt caagagtttg attgccgagg cagaggaaca accgaagagg    1080
cggagcctgg gatggagggc ttga                                           1104
```

<210> SEQ ID NO 8
<211> LENGTH: 367
<212> TYPE: PRT
<213> ORGANISM: Scytalidium thermophilum

<400> SEQUENCE: 8

```
Met Arg Ala Pro Ser Ser Val Ala Ala Thr Ala Leu Leu Leu Leu
1               5                   10                  15

Ala Thr Pro Ala Thr Ala Gln Leu His Lys Leu Ala Val Gln Ala Gly
            20                  25                  30

Leu Arg Tyr Phe Gly Ala Ala Thr Asp Thr Pro His Gln Arg Glu Arg
        35                  40                  45

Ala Pro Tyr Pro Glu Ser Tyr Pro Gln Tyr Asp Ala Ile Leu Ala Asn
    50                  55                  60

Asn Asp Glu Phe Gly Gln Thr Thr Pro Thr Asn Gly Gln Lys Trp Leu
65                  70                  75                  80

Phe Thr Glu Pro Ala Pro Arg Leu Phe Asn Phe Thr Glu Gly Asp Tyr
                85                  90                  95

Val Ala Asp Leu Ala Ala Ser Gln Gly Lys Leu Leu Arg Cys His Ala
            100                 105                 110

Leu Val Trp His Ser Gln Leu Ala Pro Trp Val Glu Thr Asn Trp
        115                 120                 125

Thr Ala Pro Ala Leu Ala Asp Ala Ile Glu Arg His Ile Arg Ala Val
    130                 135                 140

Ala Gly Tyr Tyr Arg Gly Arg Cys His Ala Trp Asp Val Val Asn Glu
145                 150                 155                 160

Ala Leu Asp Glu Asp Gly Ser Tyr Arg Gln Ser Ile Phe Tyr Arg Val
                165                 170                 175

Leu Gly Glu Glu Tyr Leu Arg Leu Ala Phe Arg Ala Ala Ala Ala
            180                 185                 190

Asp Pro Asp Ala Lys Leu Tyr Tyr Asn Asp Tyr Gly Ile Glu Arg Pro
        195                 200                 205

Thr Ser Pro Lys Thr Ala Gly Ala Leu Arg Leu Val Lys Met Leu Lys
    210                 215                 220

Asp Ala Gly Leu Arg Val Asp Gly Val Gly Met Gln Ala His Leu His
225                 230                 235                 240

Ala Asp Asn His Pro Ser Ala Glu Asp Leu Ile Ala Thr Ser Glu Ala
                245                 250                 255

Tyr Ala Glu Leu Val Asp Glu Val Ala Phe Thr Glu Leu Asp Val Arg
            260                 265                 270

Ile Lys Leu Pro Val Asp Glu Gln Lys Leu Gln Trp Gln Lys Glu Cys
        275                 280                 285

Tyr Gln Lys Val Val Thr Ala Cys Val Lys Lys Ala Cys Val Gly
    290                 295                 300

Ile Thr Leu Trp Asp Phe Tyr Asp Pro Phe Ser Trp Val Pro His Val
305                 310                 315                 320
```

```
Phe Pro Asn Asn Gly Ala Ser Leu Leu Trp Phe Glu Asp Phe Ser Lys
            325                 330                 335

His Pro Ala Tyr Asp Gly Ile Ile Glu Thr Phe Lys Ser Leu Ile Ala
        340                 345                 350

Glu Ala Glu Glu Gln Pro Lys Arg Arg Ser Leu Gly Trp Arg Ala
    355                 360                 365

<210> SEQ ID NO 9
<211> LENGTH: 1623
<212> TYPE: DNA
<213> ORGANISM: Malbranchea cinnamomea

<400> SEQUENCE: 9
atgcgcatat cactcgttct tctctccctg gtcttgagtc aggctaccct cggcctttat      60
ttgaaggata gacaagctga agtcagcctt gatgagttga tcaaggcaaa gggcaaagaa     120
tactgtggtg ttgcaaccga tagaagactt ctcacgtcca acacgaatgc ccaaattatc     180
caagccaatt tcggccaggt aaccctgag aatagcatga agtgggaatc tatccagcgt      240
atgcaacatc ctcgaaaatc tttaggacaa gttgattaaa cgctgttctt ccactgaca      300 gtctttcttt gtagcctctc agggaaactt caattggggt gacgcggact atttggtatg     360
cggaaatgtt ctcttctcac cacccgtcgc tctgaaacta aatataaacg ttaggtggat     420
tgggccacgg aaaatggcaa agttattcga ggtcatacct gggtgcgta gttgtccctg      480 accccgtcct ttggtttatg aggttgactc gagtcaaact gactgtacca gtgtggcatt     540
ctcaacttgc tggttgggtg aataacatca acgacccagc ccagctcact aaagttattc     600
aagatcatat tgctgctgtg gttggccgtt acaagggaaa aattcaccat gggtgaggc      660 ataacagttc ttcggtcaat caccctctcc ctgcgctaac cttggacata tcctaggacg     720
tcgtgaacga gatcttcaat gaagatggct cccttcgtga ctctgtgttc tcacgggtcc     780
tgggagaaga cttcgtcggt attgcattca atgctgcacg ccaagctgat ccagacgcga     840
aactctatat caacgactac aagtgagagc ctttcttatc tggtcctaag tgacgaccgt     900
tgctcatcaa acctttctca actagccttg acaatcctaa ttacgccaaa actcaggcca     960
tggccaacaa ggtgagggag tggcttgctg ctggcattcc cattgatgga attggtatgt    1020
cccatataat ttggccgagg gtccgcatag aatgactgct gactgcttga ataggcacgc    1080
aagctcatct tcagtatgga accagagtgt cttggctccg ttttcattg aattatcgag     1140 ctaacaagat ttacctaata gggccggtgg cgcaggcggc cttggaggat aagtctccct    1200
ttatgttctt tgatgacatc taaggggctg accgcccaaa acagcaattg acgttttagc    1260
gaactccggt gttgctgaag tagccatcac tgagctcgat atcgctggtg ctagcccaga    1320
cgactatgtt actgtatgca aacacgggat ccacgctggt caatactatc gcgcttgttg    1380
gggttgatgc tgacagttta ccacaggctt ttagcggctg catgggcaat gccaaatgcg    1440
ttggtgttac catctggggt gtcgctgacc cggttcgtca actcattcac tctccctgac    1500
ttgaattttg atgctgacaa ttatttttag gattcgtggc gtgcggagac gactccactg    1560
ctctttgact ataactacca gccaaagccc gcctaccacg ctgttgccca gtccttgcag    1620
tag                                                                  1623

<210> SEQ ID NO 10
<211> LENGTH: 326
<212> TYPE: PRT
<213> ORGANISM: Malbranchea cinnamomea
```

<400> SEQUENCE: 10

```
Met Arg Ile Ser Leu Val Leu Leu Ser Leu Val Leu Ser Gln Ala Thr
1               5                   10                  15

Leu Gly Leu Tyr Leu Lys Asp Arg Gln Ala Glu Val Ser Leu Asp Glu
            20                  25                  30

Leu Ile Lys Ala Lys Gly Lys Glu Tyr Cys Gly Val Ala Thr Asp Arg
        35                  40                  45

Arg Leu Leu Thr Ser Asn Thr Asn Ala Gln Ile Ile Gln Ala Asn Phe
    50                  55                  60

Gly Gln Val Thr Pro Glu Asn Ser Met Lys Trp Glu Ser Ile Gln Pro
65                  70                  75                  80

Ser Gln Gly Asn Phe Asn Trp Gly Asp Ala Asp Tyr Leu Val Asp Trp
                85                  90                  95

Ala Thr Glu Asn Gly Lys Val Ile Arg Gly His Thr Leu Val Trp His
            100                 105                 110

Ser Gln Leu Ala Gly Trp Val Asn Asn Ile Asn Asp Pro Ala Gln Leu
        115                 120                 125

Thr Lys Val Ile Gln Asp His Ile Ala Ala Val Val Gly Arg Tyr Lys
    130                 135                 140

Gly Lys Ile His His Trp Asp Val Val Asn Glu Ile Phe Asn Glu Asp
145                 150                 155                 160

Gly Ser Leu Arg Asp Ser Val Phe Ser Arg Val Leu Gly Glu Asp Phe
                165                 170                 175

Val Gly Ile Ala Phe Asn Ala Ala Arg Gln Ala Asp Pro Asp Ala Lys
            180                 185                 190

Leu Tyr Ile Asn Asp Tyr Asn Leu Asp Asn Pro Asn Tyr Ala Lys Thr
        195                 200                 205

Gln Ala Met Ala Asn Lys Val Arg Glu Trp Leu Ala Ala Gly Ile Pro
    210                 215                 220

Ile Asp Gly Ile Gly Thr Gln Ala His Leu Gln Ala Gly Gly Ala Gly
225                 230                 235                 240

Gly Leu Gly Gly Ala Ile Asp Val Leu Ala Asn Ser Gly Val Ala Glu
                245                 250                 255

Val Ala Ile Thr Glu Leu Asp Ile Ala Gly Ala Ser Pro Asp Asp Tyr
            260                 265                 270

Val Thr Ala Phe Ser Gly Cys Met Gly Asn Ala Lys Cys Val Gly Val
        275                 280                 285

Thr Ile Trp Gly Val Ala Asp Pro Asp Ser Trp Arg Ala Glu Thr Thr
    290                 295                 300

Pro Leu Leu Phe Asp Tyr Asn Tyr Gln Pro Lys Pro Ala Tyr His Ala
305                 310                 315                 320

Val Ala Gln Ser Leu Gln
                325
```

<210> SEQ ID NO 11
<211> LENGTH: 1365
<212> TYPE: DNA
<213> ORGANISM: Malbranchea cinnamomea

<400> SEQUENCE: 11

```
atggtgaagc tactcccagt catcgctgca gctctgtgcg cagtcgacgc agccattgct      60
gctcccactt ggggttggtg agcgtgtctg cacattcacc gtttgaatac agcgatgtga     120
ttatggctaa cgtttcgtcg atcgaacagg ccaagctgga actggtggaa tcgtaaaggt     180
```

```
ctgggcaatg cagctcgagc cagagggaag tactttggca cagccacgga caatatctac    240
ttgcctgaca aggcctatct ccggaagctg ttggacatca atgagtttgg gcagatcact    300
ccgtcaaaca tgctgaaggt gagcaactca aatcgtccgc actacattcc caatcgaaag    360
cactacggga gctgctgatg caaaatcttc ctgttgaacc agtgggagac cacggagcct    420
gaacagggca ggttcaattt cacaccagga gacgagcttg tcaacctggc tctgagaaac    480
ggaaaattcg tccgctgcca ctactttggtc tggcacagcc aactggctcc ctggggttag    540
cacactgcct caaactgcct cctccagatc ctgggggcag cgtacagcta acgacgaaca    600
gttgaggctc aggagtggac caatgaaact ttgatcgagg caatgacgaa ccacgtcaca    660
accgttgcga agcacttcaa gggcaggtgc tacgcttggg atgtcgtgaa tgaaggtacg    720
atgtgaagta acctatgctt cacccccaatg cctgtgggaa agcaaggcat aactgactcg    780
attccttcgc cagctttgaa cgaggacgga acattccgcg agtccatctt cctgaaggtc    840
attgggcccg agtacattcc cattgcattt gccgccgctg ctgctgccga tccccacgcg    900
aagctgtact acaacgacta caacctcgaa tggcgaagcg aaaagagcga gggcgcacgg    960
cgtatcgtca agatgatcca ggactatggc gctcgcatcg acggagtcgg gatgcaggcc    1020
cacttgattc tgggcgagac accaagcaca gaagagcaga tggccgtcat cagatcgtac    1080
accgagctag gcgttgaagt tgcatatacg gagctggata tccgcatgga actccccccg    1140
acaaaggaga agcttcggca gcagaaagaa gagtactaca cacgatccg cgcctgcgtg    1200 aagtcgtgga agtgcgtggg cgtcaccatc tgggactgga cagataagta ctcgtggatt    1260
cccgaggtgt ttgagggaga gggtgcagcg ctgccctggg acagggagct caagaagaag    1320
cctgcatact atggcattga aaggcgttc aagaagtggt tctag                    1365
```

<210> SEQ ID NO 12
<211> LENGTH: 354
<212> TYPE: PRT
<213> ORGANISM: Malbranchea cinnamomea

<400> SEQUENCE: 12

```
Met Val Lys Leu Leu Pro Val Ile Ala Ala Ala Leu Cys Ala Val Asp
1               5                   10                  15

Ala Ala Ile Ala Ala Pro Thr Trp Gly Trp Pro Ser Trp Asn Trp Trp
            20                  25                  30

Asn Arg Lys Gly Leu Gly Asn Ala Ala Arg Ala Arg Gly Lys Tyr Phe
        35                  40                  45

Gly Thr Ala Thr Asp Asn Ile Tyr Leu Pro Asp Lys Ala Tyr Leu Arg
    50                  55                  60

Lys Leu Leu Asp Ile Asn Glu Phe Gly Gln Ile Thr Pro Ser Asn Met
65                  70                  75                  80

Leu Lys Trp Glu Thr Thr Glu Pro Glu Gln Gly Arg Phe Asn Phe Thr
                85                  90                  95

Pro Gly Asp Glu Leu Val Asn Leu Ala Leu Arg Asn Gly Lys Phe Val
            100                 105                 110

Arg Cys His Thr Leu Val Trp His Ser Gln Leu Ala Pro Trp Val Glu
        115                 120                 125

Ala Gln Glu Trp Thr Asn Glu Thr Leu Ile Glu Ala Met Thr Asn His
    130                 135                 140

Val Thr Thr Val Ala Lys His Phe Lys Gly Arg Cys Tyr Ala Trp Asp
145                 150                 155                 160
```

```
Val Val Asn Glu Ala Leu Asn Glu Asp Gly Thr Phe Arg Glu Ser Ile
            165                 170                 175
Phe Leu Lys Val Ile Gly Pro Glu Tyr Ile Pro Ile Ala Phe Ala Ala
            180                 185                 190
Ala Ala Ala Ala Asp Pro His Ala Lys Leu Tyr Tyr Asn Asp Tyr Asn
            195                 200                 205
Leu Glu Trp Arg Ser Glu Lys Ser Glu Gly Ala Arg Arg Ile Val Lys
            210                 215                 220
Met Ile Gln Asp Tyr Gly Ala Arg Ile Asp Gly Val Gly Met Gln Ala
225                 230                 235                 240
His Leu Ile Leu Gly Glu Thr Pro Ser Thr Glu Glu Gln Met Ala Val
            245                 250                 255
Ile Arg Ser Tyr Thr Glu Leu Gly Val Glu Val Ala Tyr Thr Glu Leu
            260                 265                 270
Asp Ile Arg Met Glu Leu Pro Pro Thr Lys Glu Lys Leu Arg Gln Gln
            275                 280                 285
Lys Glu Glu Tyr Tyr Asn Thr Ile Arg Ala Cys Val Lys Ser Trp Lys
            290                 295                 300
Cys Val Gly Val Thr Ile Trp Asp Trp Thr Asp Lys Tyr Ser Trp Ile
305                 310                 315                 320
Pro Glu Val Phe Glu Gly Gly Ala Ala Leu Pro Trp Asp Arg Glu
            325                 330                 335
Leu Lys Lys Lys Pro Ala Tyr Tyr Gly Ile Glu Lys Ala Phe Lys Lys
            340                 345                 350
Trp Phe
```

<210> SEQ ID NO 13
<211> LENGTH: 1513
<212> TYPE: DNA
<213> ORGANISM: Corynascus thermophilus

<400> SEQUENCE: 13

```
atgcggtttt ctgcgcctct tgccctagcc ctcggcggcc tcgtggccgc gaagcccatc      60
gacatggaca gggccatgaa gtgagtgcgg acatccaagt acctcccgag tgcttagttc     120
tgtgcccatc cggccttgcc cagcagctcc cgatgtatta ttcatcaata atattaacaa     180
tggcaccatc gatggcccag gctctttcaa cggcagacgc agaccctcaa cgaggccatg     240
gtcgcctcgg gccgccagta catcggcacc gccctgaccc tccgcggcga ctacaccgag     300
gaggccatcg tcaggaccga gttcggctcc atcacgcccg agaatgccat gaagtgggac     360
gccacggagc ccaaccgcgg ccagttcacc ttcaacgcgg cggaccagca cgtcaactgg     420
gcccggcaga cgggaagca gtccgctgc cacacccctcg tgtggtactc gcagctgccc     480
ggctgggtct ccaacagcgg ctttgacaac gccacctga tcgacgtcat gtcgaaccac     540
atccgccagg tcatggggcg gtacaagggc gtctgcaccc actgggacgt ggtcaacgaa     600
ggtaagccag tcatcttggt ttttgagaca ggaaaagtaa aaaaaaaaa aggaaaagaa     660
aagaaagaa aaaagaaga agaaaagag aaaagaag aagaaaaa agaagaaaga     720
aaaaagaag aaagaaaaga gaaaaaaaaa gaaagaatga tgattgacat ggcattgga     780
aagccctcaa cgaggacggc acctaccggg acaacgtctt cctccgcgtc atcggcgagg     840
cctacatccc gatcgccttc cgcatcgcgt ccgaggcgga cccggacgcg aagctgtact     900
acaacgacta caacctcgag tacctcgggc ccaagctgga gggcgcggcg cgcatcgtcc     960
ggctggtgca gcagtacggc gtccgcatcg acggcgtcgg ataccaggcc cacctgacga    1020
```

```
ccgagtcgac gccgacgcag cagacgccca cgccgtccga ggaggacctc acggccgccc   1080
tgcgcaccac cgccgacctg ggcgtcgacg tcgcctacac cgaggttgac atccgcatgc   1140 tcaccccgc caacgagcag aagctgcagg ccctcgccgc cgcctacaac cgcctcgccc    1200
gctcctgcct caacgtcgac cgctgcgtcg gcatcaccgt ctgggtacgt ctgctgtttt   1260
ccccttcctt cccccctcg ttgttcaact tctctggcga atgagagagc ggagcggagc    1320
gaagcgggtt ggattggata aagtgaccat tgctgacccc cctcccctcc tttctgcgct   1380 catataggt gtctccgacc ggtactcgtg ggttcccaac accttctacg gcgagggcga    1440
ggccctgctc tgggacggca acttccagaa gaaggccgcc tacgacgcct tcctcgacgg   1500
catctcctcc tga                                                     1513

<210> SEQ ID NO 14
<211> LENGTH: 355
<212> TYPE: PRT
<213> ORGANISM: Corynascus thermophilus

<400> SEQUENCE: 14

Met Arg Phe Ser Ala Pro Leu Ala Leu Ala Leu Gly Gly Leu Val Ala
1               5                   10                  15

Ala Lys Pro Ile Asp Met Asp Arg Ala Met Lys Leu Phe Gln Arg Gln
            20                  25                  30

Thr Gln Thr Leu Asn Glu Ala Met Val Ala Ser Gly Arg Gln Tyr Ile
        35                  40                  45

Gly Thr Ala Leu Thr Leu Arg Gly Asp Tyr Thr Glu Glu Ala Ile Val
    50                  55                  60

Arg Thr Glu Phe Gly Ser Ile Thr Pro Glu Asn Ala Met Lys Trp Asp
65                  70                  75                  80

Ala Thr Glu Pro Asn Arg Gly Gln Phe Thr Phe Asn Ala Ala Asp Gln
                85                  90                  95

His Val Asn Trp Ala Arg Gln Asn Gly Lys Gln Val Arg Cys His Thr
            100                 105                 110

Leu Val Trp Tyr Ser Gln Leu Pro Gly Trp Val Ser Asn Ser Gly Phe
        115                 120                 125

Asp Asn Ala Thr Leu Ile Asp Val Met Ser Asn His Ile Arg Gln Val
    130                 135                 140

Met Gly Arg Tyr Lys Gly Val Cys Thr His Trp Asp Val Val Asn Glu
145                 150                 155                 160

Ala Leu Asn Glu Asp Gly Thr Tyr Arg Asp Asn Val Phe Leu Arg Val
                165                 170                 175

Ile Gly Glu Ala Tyr Ile Pro Ile Ala Phe Arg Ile Ala Ser Glu Ala
            180                 185                 190

Asp Pro Asp Ala Lys Leu Tyr Tyr Asn Asp Tyr Asn Leu Glu Tyr Leu
        195                 200                 205

Gly Pro Lys Leu Glu Gly Ala Arg Ile Val Arg Leu Val Gln Gln
    210                 215                 220

Tyr Gly Val Arg Ile Asp Gly Val Gly Tyr Gln Ala His Leu Thr Thr
225                 230                 235                 240

Glu Ser Thr Pro Thr Gln Thr Pro Thr Pro Ser Glu Glu Asp Leu
                245                 250                 255

Thr Ala Ala Leu Arg Thr Thr Ala Asp Leu Gly Val Asp Val Ala Tyr
            260                 265                 270

Thr Glu Val Asp Ile Arg Met Leu Thr Pro Ala Asn Glu Gln Lys Leu
```

```
            275                 280                 285
Gln Ala Leu Ala Ala Ala Tyr Asn Arg Leu Ala Arg Ser Cys Leu Asn
        290                 295                 300
Val Asp Arg Cys Val Gly Ile Thr Val Trp Gly Val Ser Asp Arg Tyr
305                 310                 315                 320
Ser Trp Val Pro Asn Thr Phe Tyr Gly Glu Gly Ala Leu Leu Trp
                325                 330                 335
Asp Gly Asn Phe Gln Lys Lys Ala Ala Tyr Asp Ala Phe Leu Asp Gly
            340                 345                 350
Ile Ser Ser
        355

<210> SEQ ID NO 15
<211> LENGTH: 1101
<212> TYPE: DNA
<213> ORGANISM: Corynascus thermophilus

<400> SEQUENCE: 15
atgcgactct ccgcgccctt cctcgcgtcc gcgctcctcc tcagcccggc cgcggcgcag      60
ctccacgcgc tcgcccgcaa ggccgggctc ctctacttcg gcgcggccac cgacacgccg     120
ggccagcgcg agcgggcgcc gtacccggag gcgtacccgc agtacgacgc catcttccgg     180
gacccggccg agttcgggca gacgacgccg accaacgggc agaagtggct gttcaccgag     240
ccggcgccgc ggctgttcaa cttcaccgag ggcgacgtgg tcgccgacct ggcccggtcg     300
accggcaagc tcctgcgctg ccacgccctg gtctggcaca gccagctggc gcctgggtc     360 gagcggaccg agtggacggc cgaggcgctg cgggacgcca tcgagcggca cgtccgcgcc     420
gtggccggct actaccgcgg ccgctgctac gcctgggacg tggtcaacga ggcgctcgac     480
gaggacggct cctaccgcaa gagcgtcttc tacaacgtgc tcggcgagga gtacatccgg     540
ctcgccttcc gcgccgccgc cgaggccgac ccggggcgccc ggctgtacta caacgactac     600
ggcatcgagc ggcccgactc gcccaagacc gccgcgcccc tccgcctcgt gagcatgctg     660
cgccgcgccg gcatccgcat cgacggcgtc ggcatgcagg cccacctgca cgccgacaac     720 caccctccg ccgaggacct gatcctcacc agcgagcgct acgccgccct cgtgcccgag     780
gtcgccttca ccgagctcga cgtccgcatc aagctgcccg tcaacgagac caagctcgag     840
tggcagagcg actgctacga aggtcgtg accgcctgcg tcaaggtcaa ggcctgcgtc     900
ggcatcaccc tgtgggactt ttacgacccc ttcagctggg tgcccgacac cttccccggc     960
cagggcgcct ccctgctgtg gttcgacgat ttctccaagc acccggccta tgaccgcatc    1020
gtcaagacct tcaagaagct gatccgcgag aagaagaggc cgtggttcaa tcgcaaggga    1080
aagacggtcc cggcaaacta a                                              1101

<210> SEQ ID NO 16
<211> LENGTH: 366
<212> TYPE: PRT
<213> ORGANISM: Corynascus thermophilus

<400> SEQUENCE: 16

Met Arg Leu Ser Ala Pro Phe Leu Ala Ser Ala Leu Leu Leu Ser Pro
1               5                   10                  15

Ala Ala Ala Gln Leu His Ala Leu Ala Arg Lys Ala Gly Leu Leu Tyr
            20                  25                  30

Phe Gly Ala Ala Thr Asp Thr Pro Gly Gln Arg Glu Arg Ala Pro Tyr
        35                  40                  45
```

```
Pro Glu Ala Tyr Pro Gln Tyr Asp Ala Ile Phe Arg Asp Pro Ala Glu
             50                  55                  60

Phe Gly Gln Thr Thr Pro Thr Asn Gly Gln Lys Trp Leu Phe Thr Glu
 65                  70                  75                  80

Pro Ala Pro Arg Leu Phe Asn Phe Thr Glu Gly Asp Val Val Ala Asp
                 85                  90                  95

Leu Ala Arg Ser Thr Gly Lys Leu Leu Arg Cys His Ala Leu Val Trp
                100                 105                 110

His Ser Gln Leu Ala Pro Trp Val Glu Arg Thr Glu Trp Thr Ala Glu
            115                 120                 125

Ala Leu Arg Asp Ala Ile Glu Arg His Val Arg Ala Val Ala Gly Tyr
        130                 135                 140

Tyr Arg Gly Arg Cys Tyr Ala Trp Asp Val Val Asn Glu Ala Leu Asp
145                 150                 155                 160

Glu Asp Gly Ser Tyr Arg Lys Ser Val Phe Tyr Asn Val Leu Gly Glu
                165                 170                 175

Glu Tyr Ile Arg Leu Ala Phe Arg Ala Ala Glu Ala Asp Pro Gly
            180                 185                 190

Ala Arg Leu Tyr Tyr Asn Asp Tyr Gly Ile Glu Arg Pro Asp Ser Pro
        195                 200                 205

Lys Thr Ala Gly Ala Leu Arg Leu Val Ser Met Leu Arg Arg Ala Gly
210                 215                 220

Ile Arg Ile Asp Gly Val Gly Met Gln Ala His Leu His Ala Asp Asn
225                 230                 235                 240

His Pro Ser Ala Glu Asp Leu Ile Leu Thr Ser Glu Arg Tyr Ala Arg
                245                 250                 255

Leu Val Pro Glu Val Ala Phe Thr Glu Leu Asp Val Arg Ile Lys Leu
            260                 265                 270

Pro Val Asn Glu Thr Lys Leu Glu Trp Gln Ser Asp Cys Tyr Glu Lys
        275                 280                 285

Val Val Thr Ala Cys Val Lys Val Lys Ala Cys Val Gly Ile Thr Leu
290                 295                 300

Trp Asp Phe Tyr Asp Pro Phe Ser Trp Val Pro Asp Thr Phe Pro Gly
305                 310                 315                 320

Gln Gly Ala Ser Leu Leu Trp Phe Asp Asp Phe Ser Lys His Pro Ala
                325                 330                 335

Tyr Asp Arg Ile Val Lys Thr Phe Lys Lys Leu Ile Arg Glu Lys Lys
            340                 345                 350

Arg Pro Trp Phe Asn Arg Lys Gly Lys Thr Val Pro Ala Asn
        355                 360                 365

<210> SEQ ID NO 17
<211> LENGTH: 1365
<212> TYPE: DNA
<213> ORGANISM: Corynascus thermophilus

<400> SEQUENCE: 17
atgcgtactc tcgccttcgc tctcgcggcc gccccgccg ctgttctcgc ccagtccccc      60
ctctggggcc agtgtatgcg gtttcccttc ctcccgctct gaaggagggg gacttgctct     120
cgctaaccac ctcctgcttc accataggcg gcggcattgg ctggacgggt cccacgacct     180
gcgtttctgg cgcggtgtgc caatatgtca agtcagtctt caccgcttc ctcgtttgcg      240 cctgacggcc atcccgattg ctgacacaat ctccccagcg actggtactc gcagtgcgtg     300
```

```
cccggcaatg gcggcaaccc cacgacctcc agcgctccca cctcgaccgg tggcagcggc    360
ccgactccta ctggtggcct ccatgacagg ttcaaggcca agggcaaggt ctacttcggt    420
gccgagatcg accactacca cctgaacaac aatgccttga ccaacatcgt caagaaggac    480
tttggccagg tcacgcacga aacagcctg aagtgggatg ctactgagcg taagcgacct    540
ccttcctcgc aacttgtttt gttgtatgtc ttgaagaacc acagctgacg gcgacctcga    600
tccgtagcga gccgcaacgg cttcagcttc aacaacgccg acgccgtcgt caactttgcc    660
cagtccaacg ggaagtacat ccgcggccac accctcctct ggcactctca gctgccgcag    720
tgggtgtcgc agatcaacga ccgcaacacc ctgacccagg tcatccagaa ccacgtcacc    780
accctcgtca cccgctacaa gggcaagatc ctccactggg acgtcgtcaa cgagatcttc    840
aacgaggacg gctcgctccg caacagcgtc ttcagccgcg tgctcggcga ggacttcgtc    900
ggcatcgcct tccgcgccgc tcgcgccgcc gaccccgatg ccaagctcta cattaacgac    960
tacaacctcg acatcgccaa ctacgccaag gtcaccaccg gcatggtcca gcacgtcaac   1020
aagtgggtca gccagggcat ccccatcgac ggcatcggct cccagtgcca cctggccgct   1080
cccggcggct ggaacccggc ctcgggcgtg cccgccgctc tccagaccct cgcctcggcc   1140
aacgtgaagg agatcgccat caccgagctc gacatcgccg cgccaacgc caacgactac   1200
ctcaccgtca tgaacggctg cctccaggtc tccaagtgcg tcggtatcac cgtctggggt   1260
gtctcggacc gcgacagctg cgctcgaac gactaccgc tcctcttcga cggcaactac   1320
cagcccaagg ccgcctacaa cgctctcatc aacgccctga gctaa              1365

<210> SEQ ID NO 18
<211> LENGTH: 381
<212> TYPE: PRT
<213> ORGANISM: Corynascus thermophilus

<400> SEQUENCE: 18

Met Arg Thr Leu Ala Phe Ala Leu Ala Ala Pro Ala Ala Val Leu
1               5                   10                  15

Ala Gln Ser Pro Leu Trp Gly Gln Cys Gly Gly Ile Gly Trp Thr Gly
            20                  25                  30

Pro Thr Thr Cys Val Ser Gly Ala Val Cys Gln Tyr Val Asn Asp Trp
        35                  40                  45

Tyr Ser Gln Cys Val Pro Gly Asn Gly Gly Asn Pro Thr Thr Ser Ser
    50                  55                  60

Ala Pro Thr Ser Thr Gly Gly Ser Gly Pro Thr Pro Thr Gly Gly Leu
65                  70                  75                  80

His Asp Arg Phe Lys Ala Lys Gly Lys Val Tyr Phe Gly Ala Glu Ile
                85                  90                  95

Asp His Tyr His Leu Asn Asn Asn Ala Leu Thr Asn Ile Val Lys Lys
            100                 105                 110

Asp Phe Gly Gln Val Thr His Glu Asn Ser Leu Lys Trp Asp Ala Thr
        115                 120                 125

Glu Pro Ser Arg Asn Gly Phe Ser Phe Asn Asn Ala Asp Ala Val Val
    130                 135                 140

Asn Phe Ala Gln Ser Asn Gly Lys Tyr Ile Arg Gly His Thr Leu Leu
145                 150                 155                 160

Trp His Ser Gln Leu Pro Gln Trp Val Ser Gln Ile Asn Asp Arg Asn
                165                 170                 175

Thr Leu Thr Gln Val Ile Gln Asn His Val Thr Thr Leu Val Thr Arg
            180                 185                 190
```

```
Tyr Lys Gly Lys Ile Leu His Trp Asp Val Val Asn Glu Ile Phe Asn
        195                 200                 205

Glu Asp Gly Ser Leu Arg Asn Ser Val Phe Ser Arg Val Leu Gly Glu
    210                 215                 220

Asp Phe Val Gly Ile Ala Phe Arg Ala Arg Ala Ala Asp Pro Asp
225                 230                 235                 240

Ala Lys Leu Tyr Ile Asn Asp Tyr Asn Leu Asp Ile Ala Asn Tyr Ala
            245                 250                 255

Lys Val Thr Thr Gly Met Val Gln His Val Asn Lys Trp Val Ser Gln
        260                 265                 270

Gly Ile Pro Ile Asp Gly Ile Gly Ser Gln Cys His Leu Ala Ala Pro
            275                 280                 285

Gly Gly Trp Asn Pro Ala Ser Gly Val Pro Ala Leu Gln Thr Leu
        290                 295                 300

Ala Ser Ala Asn Val Lys Glu Ile Ala Ile Thr Glu Leu Asp Ile Ala
305                 310                 315                 320

Gly Ala Asn Ala Asn Asp Tyr Leu Thr Val Met Asn Gly Cys Leu Gln
                325                 330                 335

Val Ser Lys Cys Val Gly Ile Thr Val Trp Gly Val Ser Asp Arg Asp
            340                 345                 350

Ser Trp Arg Ser Asn Asp Tyr Pro Leu Leu Phe Asp Gly Asn Tyr Gln
        355                 360                 365

Pro Lys Ala Ala Tyr Asn Ala Leu Ile Asn Ala Leu Ser
        370                 375                 380

<210> SEQ ID NO 19
<211> LENGTH: 1168
<212> TYPE: DNA
<213> ORGANISM: Penicillium oxalicum

<400> SEQUENCE: 19
atgcgctcca cgttcatggt tgcggccttg ctggccgggg cttctcaggc tgttccccat      60
tcaccttctg gcaacggcca caatgtggac ctcaataagc ttgcacagcg tcgaggactg     120
cattggtttg gcacagcagc cgatatccct ggtactgccg agactaccga tgctgcctat     180
ctgaaagttc tacgaaagaa ttttggcgaa gtgactccag cgaatgctat gaaggtatgg     240
acatatgaat ctgcataatt cacacctcgg agaggtacaa tcctacaact gtcctgctaa     300
tttggaccta tagttcatgt ataccgagcc gcaacaagac gtgttcaatt tcaccgcggc     360
tgatgaattt ttagacgtgg ccggacgcca tgggctaag attcgctgtc acaatcttgt      420
ttgggccagc caagtttctg attttgtaac ctcaaagacc tggactgcgg aggctctcac     480
ctccgtcatg aaaaaccaca tttacaagac ggtccagcac tttggtaagc gctgctactc     540
atgggatgtg gtcaacgagg ccatcaatgg agatggttcc ttctcacaga gtgtgtggta     600
caacactatc ggcgaggagt atttctatct tgctttcaag ttcgctcagg aagcattagc     660
cgagattggc gcccacgatg tgaagctgta ctacaacgac tacggcatcg agaatcaggg     720
cacaaagtcg gcgacagtac ttaagcttgt caagcaactg cgaagccgag ggctccgcat     780
tgacggcgtc ggtctcgagt cacacttcat cgttggcgaa acaccttcgt ggcggatca     840 agtggccacc aagaaagctt acattcaggc tggcctggag gtggccgtca ccgagcttga    900
catacgcttc gcacagactc cttattatac tgccgctgtt cagaagcagc aagctcaaga    960
ctactacacg agtgtgatga gttgcttgaa tgtcggtcca cgctgcatcg gtgttgttgt   1020
```

```
ctgggacttt gacgatgcct attcctgggt gcccggggca tttgccggtc aaggtggtgc      1080
ttgtttgttt aatgagactc tcgaggcaaa gcctgcattc tacgccgtgg ttgatgctct      1140 cgagggaaa gcttgcagtg tttgttaa                                          1168
```

<210> SEQ ID NO 20
<211> LENGTH: 362
<212> TYPE: PRT
<213> ORGANISM: Penicillium oxalicum

<400> SEQUENCE: 20

```
Met Arg Ser Thr Phe Met Val Ala Ala Leu Leu Ala Gly Ala Ser Gln
1               5                   10                  15

Ala Val Pro His Ser Pro Ser Gly Asn Gly His Asn Val Asp Leu Asn
            20                  25                  30

Lys Leu Ala Gln Arg Arg Gly Leu His Trp Phe Gly Thr Ala Ala Asp
        35                  40                  45

Ile Pro Gly Thr Ala Glu Thr Thr Asp Ala Ala Tyr Leu Lys Val Leu
    50                  55                  60

Arg Lys Asn Phe Gly Glu Val Thr Pro Ala Asn Ala Met Lys Phe Met
65                  70                  75                  80

Tyr Thr Glu Pro Gln Gln Asp Val Phe Asn Phe Thr Ala Ala Asp Glu
                85                  90                  95

Phe Leu Asp Val Ala Gly Arg His Gly Ala Lys Ile Arg Cys His Asn
            100                 105                 110

Leu Val Trp Ala Ser Gln Val Ser Asp Phe Val Thr Ser Lys Thr Trp
        115                 120                 125

Thr Ala Glu Ala Leu Thr Ser Val Met Lys Asn His Ile Tyr Lys Thr
    130                 135                 140

Val Gln His Phe Gly Lys Arg Cys Tyr Ser Trp Asp Val Val Asn Glu
145                 150                 155                 160

Ala Ile Asn Gly Asp Gly Ser Phe Ser Gln Ser Val Trp Tyr Asn Thr
                165                 170                 175

Ile Gly Glu Glu Tyr Phe Tyr Leu Ala Phe Lys Phe Ala Gln Glu Ala
            180                 185                 190

Leu Ala Glu Ile Gly Ala His Asp Val Lys Leu Tyr Tyr Asn Asp Tyr
        195                 200                 205

Gly Ile Glu Asn Gln Gly Thr Lys Ser Ala Thr Val Leu Lys Leu Val
    210                 215                 220

Lys Gln Leu Arg Ser Arg Gly Leu Arg Ile Asp Gly Val Gly Leu Glu
225                 230                 235                 240

Ser His Phe Ile Val Gly Glu Thr Pro Ser Leu Ala Asp Gln Val Ala
                245                 250                 255

Thr Lys Lys Ala Tyr Ile Gln Ala Gly Leu Glu Val Ala Val Thr Glu
            260                 265                 270

Leu Asp Ile Arg Phe Ala Gln Thr Pro Tyr Tyr Thr Ala Ala Val Gln
        275                 280                 285

Lys Gln Gln Ala Gln Asp Tyr Tyr Thr Ser Val Met Ser Cys Leu Asn
    290                 295                 300

Val Gly Pro Arg Cys Ile Gly Val Val Trp Asp Phe Asp Asp Ala
305                 310                 315                 320

Tyr Ser Trp Val Pro Gly Ala Phe Ala Gly Gln Gly Ala Cys Leu
                325                 330                 335

Phe Asn Glu Thr Leu Glu Ala Lys Pro Ala Phe Tyr Ala Val Val Asp
            340                 345                 350
```

Ala Leu Glu Gly Lys Ala Cys Ser Val Cys
        355                 360

<210> SEQ ID NO 21
<211> LENGTH: 981
<212> TYPE: DNA
<213> ORGANISM: Malbranchea cinnamomea

<400> SEQUENCE: 21

| | | | | | |
|---|---|---|---|---|---|
| atgcgcatat | cactcgttct | tctctccctg | gtcttgagtc | aggctaccct | cggcctttat | 60 |
| ttgaaggata | gacaagctga | agtcagcctt | gatgagttga | tcaaggcaaa | gggcaaagaa | 120 |
| tactgtggtg | ttgcaaccga | tagaagactt | ctcacgtcca | acacgaatgc | ccaaattatc | 180 |
| caagccaatt | tcggccaggt | aacccctgag | aatagcatga | agtgggaatc | tatccagccc | 240 |
| tctcagggaa | acttcaattg | gggtgacgcg | gactatttgg | tggattgggc | cacggaaaat | 300 |
| ggcaaagtta | ttcgaggtca | taccttggtg | tggcattctc | aacttgctgg | ttgggtgaat | 360 |
| aacatcaacg | acccagccca | gctcactaaa | gttattcaag | atcatattgc | tgctgtggtt | 420 |
| ggccgttaca | agggaaaaat | tcaccattgg | gacgtcgtga | acgagatctt | caatgaagat | 480 |
| ggctcccttc | gtgactctgt | gttctcacgg | gtcctgggag | aagacttcgt | cggtattgca | 540 |
| ttcaatgctg | cacgccaagc | tgatccagac | gcgaaactct | atatcaacga | ctacaacctt | 600 |
| gacaatccta | attacgccaa | aactcaggcc | atggccaaca | aggtgaggga | gtggcttgct | 660 |
| gctggcattc | ccattgatgg | aattggcacg | caagctcatc | ttcaggccgg | tggcgcaggc | 720 |
| ggccttggag | gagcaattga | cgttttagcg | aactccggtg | ttgctgaagt | agccatcact | 780 |
| gagctcgata | tcgctggtgc | tagcccagac | gactatgtta | ctgcttttag | cggctgcatg | 840 |
| ggcaatgcca | aatgcgttgg | tgttaccatc | tggggtgtcg | ctgacccgga | ttcgtggcgt | 900 |
| gcggagacga | ctccactgct | ctttgactat | aactaccagc | caaagcccgc | ctaccacgct | 960 |
| gttgcccagt | ccttgcagta | g | | | | 981 |

<210> SEQ ID NO 22
<211> LENGTH: 31
<212> TYPE: DNA
<213> ORGANISM: Humicola insolens

<400> SEQUENCE: 22
acacaactgg ggatccacca tggcgaggct c                              31

<210> SEQ ID NO 23
<211> LENGTH: 37
<212> TYPE: DNA
<213> ORGANISM: Humicola insolens

<400> SEQUENCE: 23
gtcaccctct agatctcgac ccccaaagaa atgggta                         37

<210> SEQ ID NO 24
<211> LENGTH: 34
<212> TYPE: DNA
<213> ORGANISM: Humicola insolens

<400> SEQUENCE: 24
acacaactgg ggatccacca tgcgtttctc cgcc                            34

<210> SEQ ID NO 25
<211> LENGTH: 38

```
<212> TYPE: DNA
<213> ORGANISM: Humicola insolens

<400> SEQUENCE: 25
gtcaccctct agatctaaat tgcggtcaca gagtccag                              38

<210> SEQ ID NO 26
<211> LENGTH: 38
<212> TYPE: DNA
<213> ORGANISM: Humicola insolens

<400> SEQUENCE: 26
acacaactgg ggatccacca tgcatctcgc ttcgtcgc                              38

<210> SEQ ID NO 27
<211> LENGTH: 36
<212> TYPE: DNA
<213> ORGANISM: Humicola insolens

<400> SEQUENCE: 27
gtcaccctct agatctaagt ctccacccgc atcgac                                36

<210> SEQ ID NO 28
<211> LENGTH: 33
<212> TYPE: DNA
<213> ORGANISM: Humicola insolens

<400> SEQUENCE: 28
acacaactgg ggatccacca tgagagctcc gtc                                   33

<210> SEQ ID NO 29
<211> LENGTH: 40
<212> TYPE: DNA
<213> ORGANISM: Humicola insolens

<400> SEQUENCE: 29
gtcaccctct agatctgaca aatcttcaca cagcccaatg                            40

<210> SEQ ID NO 30
<211> LENGTH: 41
<212> TYPE: DNA
<213> ORGANISM: Malbranchea cinnamomea

<400> SEQUENCE: 30
acacaactgg ggatccacca tgcgcatatc actcgttctt c                          41

<210> SEQ ID NO 31
<211> LENGTH: 39
<212> TYPE: DNA
<213> ORGANISM: Malbranchea cinnamomea

<400> SEQUENCE: 31
gtcaccctct agatctctac tgcaaggact gggcaacag                             39

<210> SEQ ID NO 32
<211> LENGTH: 44
<212> TYPE: DNA
<213> ORGANISM: Malbranchea cinnamomea

<400> SEQUENCE: 32
acacaactgg ggatccacca tggtgaagct actcccagtc atcg                       44

<210> SEQ ID NO 33
```

```
<211> LENGTH: 38
<212> TYPE: DNA
<213> ORGANISM: Malbranchea cinnamomea

<400> SEQUENCE: 33
gtcaccctct agatctcgcc aacagatcct aatgggac                              38

<210> SEQ ID NO 34
<211> LENGTH: 38
<212> TYPE: DNA
<213> ORGANISM: Corynascus thermophilus

<400> SEQUENCE: 34
acacaactgg ggatccacca tgcggttttc tgcgcctc                              38

<210> SEQ ID NO 35
<211> LENGTH: 39
<212> TYPE: DNA
<213> ORGANISM: Corynascus thermophilus

<400> SEQUENCE: 35
gtcaccctct agatctaccg tccaccgttc ctcttagag                             39

<210> SEQ ID NO 36
<211> LENGTH: 34
<212> TYPE: DNA
<213> ORGANISM: Corynascus thermophilus

<400> SEQUENCE: 36
acacaactgg ggatccacca tgcgactctc cgcg                                  34

<210> SEQ ID NO 37
<211> LENGTH: 35
<212> TYPE: DNA
<213> ORGANISM: Corynascus thermophilus

<400> SEQUENCE: 37
gtcaccctct agatctcaca ggttgggggg atgag                                 35

<210> SEQ ID NO 38
<211> LENGTH: 38
<212> TYPE: DNA
<213> ORGANISM: Corynascus thermophilus

<400> SEQUENCE: 38
acacaactgg ggatccacca tgcgtactct cgccttcg                              38

<210> SEQ ID NO 39
<211> LENGTH: 37
<212> TYPE: DNA
<213> ORGANISM: Corynascus thermophilus

<400> SEQUENCE: 39
gtcaccctct agatctaccc atccatcaca atcacac                               37

<210> SEQ ID NO 40
<211> LENGTH: 38
<212> TYPE: DNA
<213> ORGANISM: Penicillium oxalicum

<400> SEQUENCE: 40
acacaactgg ggatccacca tgcgctccac gttcatgg                              38
```

```
<210> SEQ ID NO 41
<211> LENGTH: 43
<212> TYPE: DNA
<213> ORGANISM: Penicillium oxalicum

<400> SEQUENCE: 41
gtcaccctct agatctgaag catcctctag tgaggcctat caa            43
```